United States Patent
Ohta

(10) Patent No.: US 9,587,224 B2
(45) Date of Patent: Mar. 7, 2017

(54) METHOD FOR PRODUCING PLURIPOTENT CELL USING BACTERIUM HAVING FERMENTATION ABILITY

(75) Inventor: Kunimasa Ohta, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 243 days.

(21) Appl. No.: 14/131,498

(22) PCT Filed: Jul. 10, 2012

(86) PCT No.: PCT/JP2012/067544
§ 371 (c)(1),
(2), (4) Date: May 5, 2014

(87) PCT Pub. No.: WO2013/008803
PCT Pub. Date: Jan. 17, 2013

(65) Prior Publication Data
US 2014/0255942 A1  Sep. 11, 2014

(30) Foreign Application Priority Data

Jul. 11, 2011  (JP) ................. 2011-152479
May 9, 2012  (JP) ................. 2012-107210

(51) Int. Cl.
| | | |
|---|---|---|
| C12N 15/00 | (2006.01) |
| C12N 5/074 | (2010.01) |
| C12P 39/00 | (2006.01) |
| C12N 1/38 | (2006.01) |
| G01N 33/50 | (2006.01) |
| A61K 35/744 | (2015.01) |
| A61K 35/747 | (2015.01) |

(52) U.S. Cl.
CPC .......... *C12N 5/0696* (2013.01); *A61K 35/744* (2013.01); *A61K 35/747* (2013.01); *C12N 1/38* (2013.01); *C12P 39/00* (2013.01); *G01N 33/5011* (2013.01); *C12N 2500/72* (2013.01); *C12N 2502/70* (2013.01)

(58) Field of Classification Search
CPC .................................................. C12N 5/0696
See application file for complete search history.

(56) References Cited

U.S. PATENT DOCUMENTS

| | | |
|---|---|---|
| 2005/0158292 A1 | 7/2005 | Tsuji et al. |
| 2006/0222636 A1 | 10/2006 | Rambukkana |
| 2008/0219957 A1 | 9/2008 | Lim et al. |
| 2010/0305041 A1 | 12/2010 | Jo et al. |
| 2011/0269165 A1 | 11/2011 | Tsuji et al. |

FOREIGN PATENT DOCUMENTS

| | | |
|---|---|---|
| EP | 1082964 A1 | 3/2001 |
| JP | 9-30981 | 2/1997 |
| JP | 2004-248505 A | 9/2004 |
| JP | 2005-97280 A | 4/2005 |
| JP | 2005/154387 A | 6/2005 |
| WO | 99/64023 A1 | 12/1999 |
| WO | 02/097065 A2 | 12/2002 |
| WO | 2004/016772 A1 | 2/2004 |
| WO | 2004/087218 A1 | 10/2004 |
| WO | 2005/033297 | 4/2005 |
| WO | 2007/026255 A2 | 3/2007 |
| WO | 2007/027156 A1 | 3/2007 |
| WO | 2009/031836 A1 | 3/2009 |
| WO | 2010/069920 A1 | 6/2010 |
| WO | 2011/049099 A1 | 4/2011 |

OTHER PUBLICATIONS

Bi, 2010, BMC Cell Biology, 11:46, pp. 1-7.*
Thomson et al. (PNAS, 92:7844-7848 (Aug. 1995)).*
NIH (Stem Cells: Scientific Progress and Future Research Directions, Department of Health and Human Services, Chapter 1, pp. 14, Jun. 2001).*
Djuric and Ellis, 202, Stem Cell Research and Therapy, 2010,1:3, pp. 1-6.*
Schiffrin (1997, Am J Clin Nutr, 66:515S-520S).*
Ito (2015, Dev. Growth and Differentiation, 57:305-312.*
Mohamadzadeh (PNAS; 2005,102:2880-2885).*
Paolillo (International Immunopharmacology, 200, 9:1265-1271).*
Ohta (2012, PLoS One, 7:12. E51866, pp. 1-10.*
Dunne, Microbbial Ecology in Health and Disease, 2004, 16:96-104.*
Chou (2008, Cell, 135:449-461).*
Wagnerova et al., "In vivo reprogramming in inflammatory bowel disease", *Gene Therapy*, vol. 20, No. 12, pp. 1111-1118, published online Sep. 12, 2013.
Seow et al., "*Lactobacillus rhamnosus* GG induces tumor regression in mice bearing orthotopic bladder tumors", *Cancer Science*, vol. 101, No. 3, pp. 751-758, published online Dec. 14, 2009.
Extended European Search Report for EP Patent Application No. 12811861.9, dated Aug. 29, 2014.
Takahashi and Yamanaka, Cell 126, 663-676, 2006.
Takahashi et al., Cell 131, 861-872, 2007.

(Continued)

*Primary Examiner* — Valarie Bertoglio
(74) *Attorney, Agent, or Firm* — Greenblum & Bernstein, P.L.C.

(57) ABSTRACT

It is an object of the present invention to provide a method for producing pluripotent cells that are free of the risk of cellular canceration and that can be applied to regenerative medicine with a high degree of safety. The present invention provides a method for producing pluripotent cells from somatic cells comprising a step of bringing bacteria having fermentation ability or a component or secretory product thereof into contact with somatic cells.

6 Claims, 11 Drawing Sheets

(56) References Cited

OTHER PUBLICATIONS

International Search Report for PCT/JP2012/067544, mailed Aug. 7, 2012.
International Preliminary Report on Patentability for PCT/JP2012/067544 mailed Jan. 16, 2014.
Office Action issued in European Patent Office Application No. 12 811 861.9, dated Mar. 8, 2016.

* cited by examiner

cell mass 8 days after the initiation of culture

# METHOD FOR PRODUCING PLURIPOTENT CELL USING BACTERIUM HAVING FERMENTATION ABILITY

TECHNICAL FIELD

The present invention relates to a method for producing pluripotent cells using bacteria having fermentation ability.

BACKGROUND ART

ES cells are embryonic stem cells that were discovered in mouse embryos in 1981 and in human embryos in 1998. ES cells having the ability to develop into a variety of types of cells (i.e., pluripotent cells) except for the cells that constitute placenta have been primarily studied for the construction of tissues or organs therefrom. Because of the use of the fertilized eggs that would develop into new lives if they were allowed to grow smoothly, ES cells raise serious ethical questions. Another serious issue is the problem of rejection. When differentiated cells or organs prepared from ES cells are transplanted into a patient, the immune system of the patient may recognize such cells or organs as foreign substances and attack them.

In order to overcome the problems of ES cells, Professor Shinya Yamanaka et al. at Kyoto University developed cells capable of developing into various types of cells from dermal cells that are not generally differentiated into cells exerting other functions, and they designated these cells "iPS cells." They demonstrated that introduction of four factors referred to as "Yamanaka factors;" i.e., Oct 3/4, Sox2, Klf4, and c-Myc, into mouse or human dermal cells with the use of a retrovirus vector would lead to reprogramming of cells and production of pluripotent cells, as is the case with ES cells (Non-Patent Document 1: Takahashi and Yamanaka, Cell 126, 663-676, 2006; and Non-Patent Document 2: Takahashi et al., Cell 131, 861-872, 2007). Since the cells used in such case are derived from somatic cells, such as differentiated dermal cells, of the patient him/herself, the immune system would recognize an organ prepared from the cells differentiated from the iPS cells as an autonomous organ upon transplantation thereof, and the transplant would accordingly not be rejected. As a result of the discovery of iPS cells, the issue of ethical concern regarding ES cells was overcome.

As described above, iPS cells have drawn attention worldwide as a powerful tool for regenerative medicine, although the technical problem of canceration of cells remains problematic. A cause of canceration is related to the introduction of the c-Myc gene into cells; however, iPS cells have been produced from the other 3 factors than the c-Myc gene in recent years. When introducing a gene into a cell, iPS cells were prepared with the use of the adenovirus or plasmid vector instead of the retrovirus vector. This allowed for the production of iPS cells with advanced safety and usefulness. However, this technique involves the artificial and forced expression of several genes in cells that had completed differentiation, and the risk that such cells would experience canceration in the future cannot be denied.

Meanwhile, Patent Document 1 describes a method of using *Mycobacterium leprae* or a component thereof so as to produce reprogrammed embryonic stem (ES)-like cells. Specifically, Patent Document 1 describes a method for producing reprogrammed ES-like cells comprising bringing *Mycobacterium leprae* or a component thereof into contact with a differentiated cell derived from an adult, and it also describes cells produced by such method. However, *Mycobacterium leprae* is a *lepra bacillus*, and application thereof to regenerative medicine remains problematic in terms of safety.

PRIOR ART DOCUMENTS

Non-Patent Documents

Non-Patent Document 1: Takahashi and Yamanaka, Cell 126, 663-676, 2006
Non-Patent Document 2: Takahashi et al., Cell 131, 861-872, 2007

Patent Documents

Patent Document 1: US Patent Application No. 2006/0222636 A1

DISCLOSURE OF THE INVENTION

Object to be Solved by the Invention

As described above, embryonic stem (ES) cells that can be obtained during the process of the development of fertilized eggs into embryos or induced pluripotent stem (iPS) cells obtained from one's own body are pluripotent stem cells that can grow into substantially any type of tissue in the future. While the applicability of such cells to treatment of intractable diseases has been expected, these cells remain problematic in terms of ethical concerns and canceration risk. Accordingly, it is an object of the present invention to provide a method for producing pluripotent cells that are free of the risk of cellular canceration and that can be applied to regenerative medicine with a high degree of safety.

Means for Solving the Object

In order to attain the above object, the present inventor focused on bacteria having fermentation ability, such as lactic acid bacteria and *Bacillus subtilis* var *natto*, and inspected the correlations between such bacteria and cells. Specifically, the present inventor confirmed that the human dermal fibroblasts (HDFs) that had completed differentiation (Cell Applications, Inc., Cat No. 106-05a) would form cell masses, as in the case of ES cells or iPS cells, upon infection with lactic acid bacteria (i.e., *Lactococcus lactis* subsp. *lactis* (JCM20101), *Streptococcus salivarius* subsp. *thermophilus* (JCM20026), and *Lactobacillus* sp. (JCM20061), Japan Collection of Microorganisms, RIKEN BioResource Center), or *Bacillus subtilis* var. *natto*, and that such cell masses could be stained with alkaline phosphatase. In addition, these cell masses were found to express marker molecules (SSEA-4) that could be expressed specifically in ES cells or iPS cells. Further, these cell masses were found to differentiate into cells of the mesoderm or ectoderm. In general, pluripotent stem cells induced by lactic acid bacteria that are present in a human body may be used to overcome the problems of ethical concerns and canceration, and the use of such pluripotent stem cells enables the production of pluripotent cells that are applicable to regenerative medicine with a high degree of safety. The pluripotent cells produced by the method of the present invention can serve as useful materials for regenerative medicine in the treatment of diseases that were impossible to cure in the past. In the present invention, further, the endosymbiotic theory proposed by Margulis in 1970 (i.e., anaerobic eukaryotes ingested aerobic bacteria to realize the symbiotic conditions and then evolved into the eukaryocytes of the current conditions) was experimentally verified, and the origin of eukaryocytes having organelles that independently generate energy, such as mitochondria or chloroplast, can thereby be expected to be elucidated. The present invention had been completed on the basis of the above findings.

The present invention provides the following invention.

(1) A method for producing pluripotent cells from somatic cells comprising a step of bringing bacteria having fermentation ability or a component or secretory product thereof into contact with somatic cells.
(2) The method according to (1), wherein the somatic cells are somatic cells derived from a mammalian.
(3) The method according to (1) or (2), wherein the somatic cells are somatic cells derived from a human or mouse.
(4) The method according to any one of (1) to (3), wherein the somatic cells are cancer cells.
(5) The method according to any one of (1) to (4), wherein the bacteria having fermentation ability are lactic acid bacteria or *Bacillus subtilis* var. *natto*.
(6) The method according to (5), wherein the lactic acid bacteria belong to the genus *Lactococcus, Streptococcus*, or *Lactobacillus*.
(7) The method according to (6), wherein the lactic acid bacteria are *Lactococcus lactic* subsp. *Lactis, Streptococcus salivarius* subsp. *thermophilus, Lactobacillus* sp., or *Lactobacillus acidophilus*.
(8) The method according to any one of (1) to (7), wherein the step of bringing bacteria having fermentation ability or a component or secretory product thereof into contact with the somatic cells is a step of infecting the somatic cells with bacteria having fermentation ability or a component or secretory product thereof.
(9) The method according to any one of (1) to (8), which comprises a step of treating somatic cells with trypsin before bacteria having fermentation ability or a component or secretory product thereof are brought into contact with the somatic cells.
(10) A pluripotent cell, which can be produced by the method according to any one of (1) to (9).
(11) A method for producing somatic cells which were induced to differentiate from pluripotent cells which comprises the steps of:
(a) producing pluripotent cells by the method according to any one of (1) to (9); and
(b) inducing the pluripotent cells produced in step (a) to differentiate.
(12) A somatic cell which was induced to differentiate from pluripotent cells, which can be obtained by the method according to (11).
(13) A kit used for producing pluripotent cells from somatic cells, which comprises bacteria having fermentation ability or a component or secretory product thereof.
(14) A method for producing non-cancer cells from cancer cells, which comprises a step of bringing bacteria having fermentation ability or a component or secretory product thereof into contact with cancer cells.
(15) The method according to (14), wherein the cancer cells are human cancer cells.
(16) The method according to (14) or (15), wherein the bacteria having fermentation ability are lactic acid bacteria or *Bacillus subtilis* var. *natto*.
(17) The method according to (16), wherein the lactic acid bacteria belong to the genus *Lactococcus, Streptococcus*, or *Lactobacillus*.
(18) The method according to (17), wherein the lactic acid bacteria are *Lactococcus lactis* subsp. *Lactis, Streptococcus salivarius* subsp. *thermophilus, Lactobacillus* sp., or *Lactobacillus acidophilus*.
(19) The method according to any one of (14) to (18), wherein the step of bringing bacteria having fermentation ability or a component or secretory product thereof into contact with the cancer cells is a step of infecting the cancer cells with bacteria having fermentation ability or a component or secretory product thereof.
(20) An non-cancer cell which can be produced by the method according to any one of (14) to (19).
(21) An anti-cancer agent comprising lactic acid bacteria or a component or secretory product thereof.
(22) The anti-cancer agent according to (21), wherein the lactic acid bacteria belong to the genus *Lactococcus, Streptococcus*, or *Lactobacillus*.
(23) The anti-cancer agent according to (21) or (22), wherein the lactic acid bacteria are *Lactococcus lactis* subsp. *Lactis, Streptococcus salivarius* subsp. *thermophilus, Lactobacillus* sp., or *Lactobacillus acidophilus*.
(24) A method for screening for an anti-cancer component derived from lactic acid bacteria, which comprises a step of bringing lactic acid bacteria or a component or secretory product thereof into contact with cancer cells and a step of measuring the extent of conversion of cancer cells into non-cancer cells.
(25) The method according to (24), wherein the lactic acid bacteria belong to the genus *Lactococcus, Streptococcus*, or *Lactobacillus*.
(26) The method according to (24) or (25), wherein the lactic acid bacteria are *Lactococcus lactis* subsp. *Lactis, Streptococcus salivarius* subsp. *thermophilus, Lactobacillus* sp., or *Lactobacillus acidophilus*.

Effects of the Invention

According to the present invention, bacteria having fermentation ability, such as lactic acid bacteria, that coexist with cells in the human body are allowed to infect somatic cells, and pluripotent stem cells can then be produced. Since the method of the present invention does not require any artificial gene introduction procedure, the risk of canceration occurring in the produced pluripotent cells can be substantially equivalent to that in the normal state. The method for producing pluripotent cells according to the present invention that involves the use of bacteria having fermentation ability, such as lactic acid bacteria, is useful in the medical field (including drug discovery research and testing of safety, efficacy, and side effects of pharmaceutical products), disease research (elucidation of cause and development regarding therapeutic and preventive methods for intractable diseases), regenerative medicine (restoration of neurological, vascular, and organ functions), and the food industry.

EMBODIMENTS FOR CARRYING OUT THE INVENTION

Figure 1:
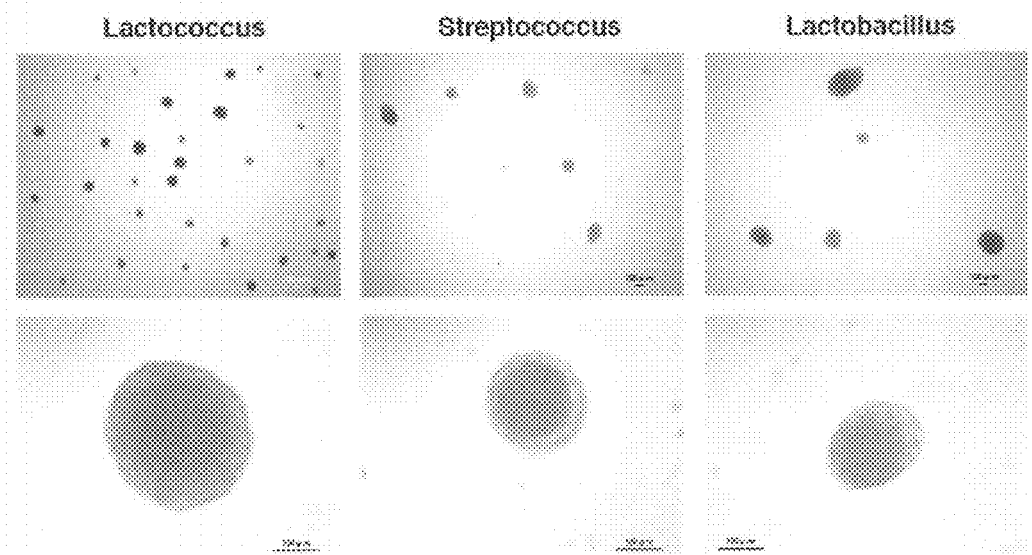
FIG. 1 shows HDF cells cultured together with lactic acid bacteria.

Hereafter, the present invention is described in greater detail.

The method for producing pluripotent cells from somatic cells according to the present invention is characterized by a step comprising bringing bacteria having fermentation ability or a component or secretory product thereof into contact with somatic cells.

In the present invention, any somatic cells can be used for reprogramming, without particular limitation. Specifically, the term "somatic cells" used in the present invention refers to any cells which constitute an organism, except for germ cells. Differentiated somatic cells or undifferentiated stem cells may be used. Somatic cells may originate from any organisms, such as mammalians, birds, fish, reptiles, or amphibians, without particular limitation, with mammalians (e.g., rodents such as mice or primates such as humans) being preferable, and humans or mice being particularly preferable. When human somatic cells are used, such somatic cells may be derived from an embryo, a newborn, or an adult. When the pluripotent cells produced by the method of the present invention are used for the treatment of a disease in the field of regenerative medicine, the use of somatic cells isolated from a patient with the disease of interest is preferable. In the present invention, cancer cells can be used as somatic cells. By bringing bacteria having fermentation ability or a component or secretory product thereof into contact with cancer cells, non-cancer cells can be produced from the cancer cells. In the present invention, a step of bringing bacteria having fermentation ability or a component or secretory product thereof into contact with somatic cells (including cancer cells) can be carried out in vitro.

The term "pluripotent cells" used in the present invention refers to cells capable of autonomous replication under particular culture conditions (specifically in the presence of lactic acid bacteria) for a long period of time and capable of differentiating into a plurality of types of cells (e.g., ectoderm, mesoderm, or endoderm cells) under particular differentiation-inducing conditions, and these cells may also be referred to as "stem cells."

In the present invention, bacteria having fermentation ability or a component or secretory product thereof are brought into contact with somatic cells.

Bacteria having fermentation ability used in the present invention are not particularly limited. Aerobic bacteria, such as lactic acid bacteria or *Bacillus subtilis* var *natto*, or anaerobic bacteria, such as *Bifidobacterium*, may be used.

Lactic acid bacteria used in the present invention are not particularly limited. The term "lactic acid bacteria" is a generic term for bacteria capable of producing lactic acid from a saccharide via fermentation. Representative examples of lactic acid bacteria include those belonging to the genera *Lactobacillus, Bifidobacterium, Enterococcus, Lactococcus, Pediococcus, Leuconostoc,* and *Streptococcus,* and such lactic acid bacteria can be used in the present invention. Use of lactic acid bacteria belonging to the genus *Lactococcus, Streptococcus,* or *Lactobacillus* is preferable. Use of *Lactococcus lactis* subsp. *Lactis, Streptococcus salivarius* subsp. *thermophilus, Lactobacillus* sp., or *Lactobacillus acidophilus* is particularly preferable.

Examples of components of bacteria having fermentation ability include, but are not limited to, a cell wall, a nucleic acid, a protein, a cell organelle, a lipid, a sugar, a carbohydrate, a glucolipid, and a glycosylated sugar.

In the present invention, culture is conducted in the presence of bacteria having fermentation ability with the use of a common medium for cell culture. Thus, pluripotent cells or non-cancer cells according to the present invention can be separated and cultured. According to need, various growth factors, cytokines, or hormones (e.g., components associated with proliferation and maintenance of human ES cells, such as FGF-2, TGFβ-1, activin A, Noggin, BDNF, NGF, NT-1, NT-2, or NT-3) may be added to a medium used for culturing the pluripotent cells of the present invention. Moreover, the differentiation potency and proliferation potency of the separated pluripotent cells can be verified by a method of confirmation known with respect to ES cells.

The applications of the pluripotent cells and the non-cancer cells produced by the method of the present invention are not particularly limited, and these cells can be used for various types of testing, research, or disease treatments, or for other purposes. For example, the pluripotent cells produced by the method of the present invention can be treated with a growth factor, such as retinoic acid or EGF, or with glucocorticoid to induce differentiation into cells of interest (e.g., nerve cells, cardiac muscle cells, hepatic cells, pancreatic cells, or blood cells). The differentiated cells thus obtained can be returned to the patient's body, so as to realize stem cell therapy by autologous cell transplantation.

Examples of central nervous system diseases that can be treated with the use of the pluripotent cells of the present invention include Parkinson's disease, Alzheimer's disease, multiple sclerosis, cerebral infarction, and spinal injury. For the treatment of Parkinson's disease, the pluripotent cells are differentiated into dopaminergic neurons and then transplanted intrastriatally to the patient with Parkinson's disease. Differentiation into dopaminergic neurons can be carried out via coculture of the mouse stroma cell line (PA6 cells) and the pluripotent cells of the present invention under serum-free conditions. For the treatment of Alzheimer's disease, cerebral infarction, and spinal injury, the pluripotent cells of the present invention may be induced to differentiate into neural stem cells and then transplanted into the site of a lesion.

Also, the pluripotent cells of the present invention can be used for the treatment of hepatic diseases, such as hepatitis, cirrhosis, or liver failure. For the treatment of such diseases, the pluripotent cells of the present invention may be differentiated into hepatic cells or hepatic stem cells and then transplanted. The pluripotent cells of the present invention may be cultured in the presence of activin A for 5 days, and culture may be further conducted for about 1 week in the presence of the hepatic cell growth factor (HGF). Thus, hepatic cells or hepatic stem cells can be obtained.

Further, the pluripotent cells of the present invention can be used for the treatment of pancreatic disorders, such as type I diabetes mellitus. In the case of type I diabetes mellitus, the pluripotent cells of the present invention may be differentiated into pancreatic β cells and transplanted into the pancreas. The pluripotent cells of the present invention can be differentiated into pancreatic β cells in accordance with a method of differentiating ES cells into pancreatic β cells.

Further, the pluripotent cells of the present invention can be used for the treatment of cardiac failure associated with ischemic heart diseases. For the treatment of cardiac failure, it is preferable that the pluripotent cells of the present invention be differentiated into cardiac muscle cells and then transplanted into the site of a lesion. By adding Noggin to a medium 3 days before an embryoid body is formed, the pluripotent cells of the present invention can be differentiated into cardiac muscle cells about 2 weeks after the embryoid body is formed.

According to the present invention, bacteria having fermentation ability (e.g., lactic acid bacteria) or a component or secretory product thereof are brought into contact with cancer cells, and non-cancer cells can then be produced from the cancer cells. Accordingly, the lactic acid bacteria, or a component or secretory product thereof, are useful as an anti-cancer agent, and the present invention can provide an anti-cancer agent which comprises lactic acid bacteria or a component or secretory product thereof.

According to the present invention, further, lactic acid bacteria or a component or secretory product thereof are brought into contact with cancer cells, the extent of conversion of cancer cells into non-cancer cells is assayed, and anti-cancer components originating from lactic acid bacteria can then be screened for. The anti-cancer components originating from lactic acid bacteria that are identified by the above-described screening method are useful as anti-cancer agents.

The present invention is described in greater detail with reference to the following examples, although the technical scope of the present invention is not limited to these examples.

EXAMPLES

Example 1

Human dermal fibroblasts (HDF cells) (Cell Applications, Inc., Cat No. 106-05a) were cultured in a fibroblast growth medium (Cell Applications, Inc.) in a 10-cm petri dish. The cells were washed with 10 ml of CMF ($Ca^{2+}$ $Mg^{2+}$-free buffer). A 0.25% trypsin solution (containing 1 mM EDTA) was added in an amount of 1 ml and allowed to spread across and throughout the dish. The cells were introduced into a $CO_2$ incubator (37° C.) and allowed to stand therein for 5 minutes. A trypsin inhibitor solution (3 ml, Cell Applications, Inc.) was added to prepare a cell suspension, and the number of the cells was counted. Lactic acid bacteria (i.e., *Lactococcus lactis* subsp. *Lactis* (JCM20101), *Streptococcus salivarius* subsp. *thermophilus* (JCM20026), *Lactobacillus* sp. (JCM20061), or *Lactobacillus acidophilus* (JCM1021)) were introduced into a 6-well plate at $7 \times 10^7$ cells/well in advance, and the HDF cells were then added ($5 \times 10^5$ cells/2 ml). Lactic acid bacteria purchased from the Japan Collection of Microorganisms of the RIKEN BioResource Center were used. The cells were cultured in that state in an incubator at 34° C. in the presence of 5% $CO_2$.

As a result, cell masses were observed several days later. The photographs shown in FIG. 1 show the conditions 8 days after the initiation of culture.

Example 2

HDF cells ($5 \times 10^5$ cells/2 ml) were infected with lactic acid bacteria ($7 \times 10^7$ cells) (i.e., *Lactococcus lactis* subsp. *Lactis* (JCM20101), *Streptococcus salivarius* subsp. *thermophilus* (JCM20026), or *Lactobacillus* sp. (JCM20061)) in a 6-well plate, culture was conducted in an incubator at 34° C. in the presence of 5% $CO_2$ for 8 days, the resulting cell masses were transferred to a 4-well plate, the plate was introduced into an alkaline phosphatase coloring solution (Roche), and color was allowed to develop at room temperature for 1 hour.

Figure 2:
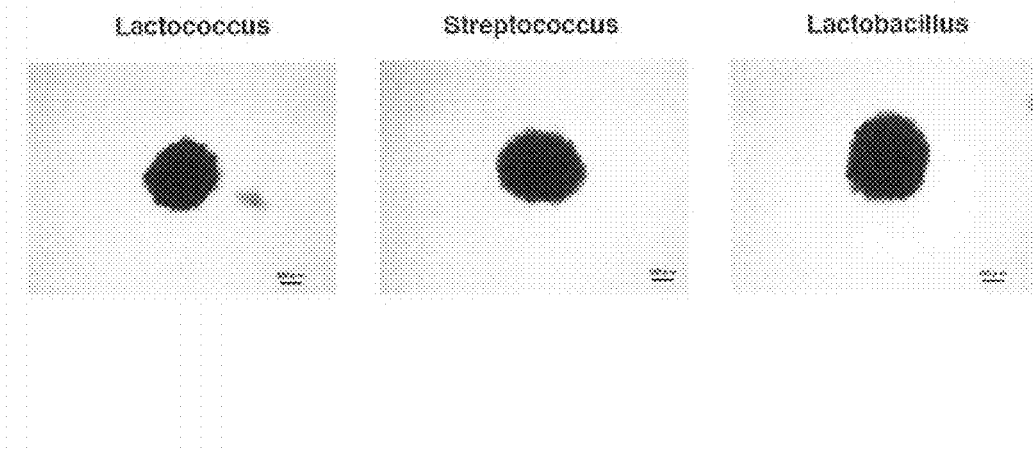
FIG. 2 shows the results of staining attained by infecting the HDF cells with lactic acid bacteria and staining the formed cell mass with an alkaline phosphatase coloring solution.

As a result, the cell masses turned purple, as shown in FIG. 2. This indicates that the HDF cells infected with lactic acid bacteria are pluripotent.

Example 3

HDF cells ($5\times10^5$ cells/2 ml) were infected with lactic acid bacteria ($7\times10^7$ cells) (i.e., *Lactococcus lactis* subsp. *Lactis* (JCM20101)) in a 6-well plate, culture was conducted in an incubator at 34° C. in the presence of 5% $CO_2$ for 8 days, and the formed cell mass was fixed with 4% PFA at room temperature for 15 minutes, followed by staining thereof with a mouse anti-SSEA-4 antibody (MILLIPORE).

Figure 3:
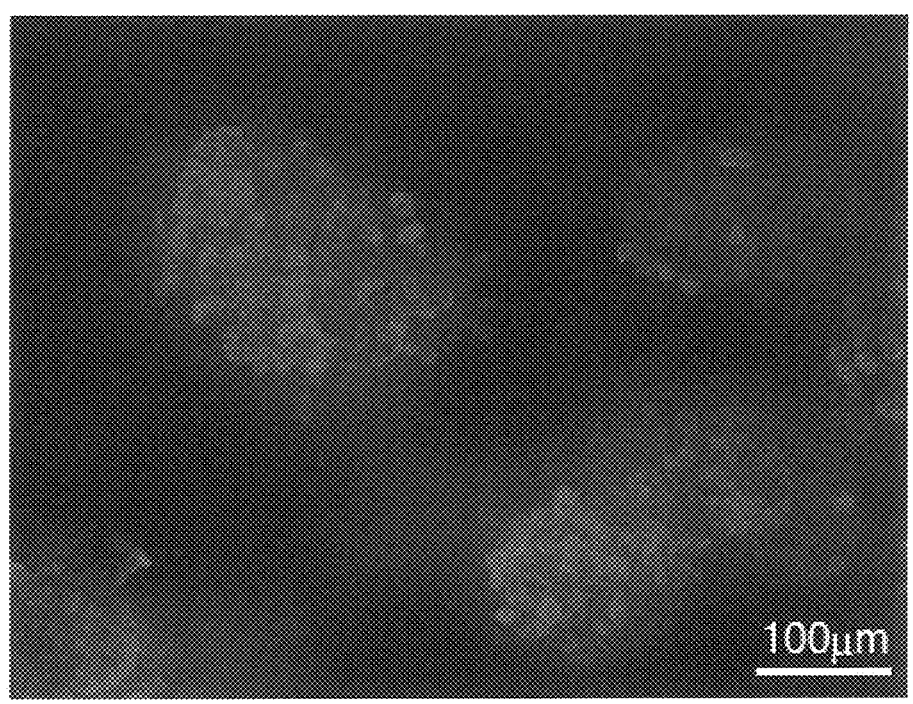
FIG. 3 shows the results of staining attained by infecting the HDF cells with lactic acid bacteria and staining the formed cell mass with anti-SSEA-4 antibody (MILLIPORE).
Figure 4:
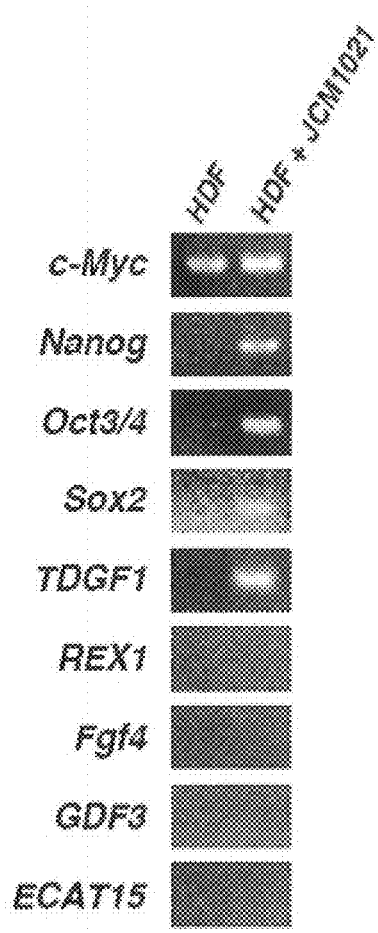
FIG. 4 shows the results obtained by infecting the HDF cells with lactic acid bacteria and subjecting cDNA derived from the formed cell mass to RT-PCR.

As a result, the cell mass was found to express the SSEA-4 antigen, which would be expressed specifically by pluripotent cells, as shown in FIG. 3.

Example 4

HDF cells ($2\times10^5$/ml) were seeded on a 12-well plate, infected with lactic acid bacteria ($2\times10^7$ cells) (i.e., *Lactobacillus acidophilus* (JCM1021)), and cultured in an incubator at 34° C. in the presence of 5% $CO_2$ for 8 days. Half of the culture solution was exchanged every 5 days, and tRNA was purified from the 20 formed cell masses with the use of a Trizol reagent (Invitrogen) 2 weeks later.

cDNA was synthesized with the use of Oligo (dT) primer and SuperScript™ III (Invitrogen), and RT-PCR was carried out with the use of a set of primers for several genes reported to be associated with pluripotency. The amplified DNA was subjected to 2% agarose gel electrophoresis, and a band was detected via ethidium bromide staining.

As a result, induction of the expression of c-Myc, Nanog, Oct3/4, Sox2, and TDGF1, which were not expressed in the HDF cells, was observed in the cell masses infected with lactic acid bacteria, although expression of REX1, Fgf4, GDF3 or ECAT16 was not observed.

Example 5

Figure 5:
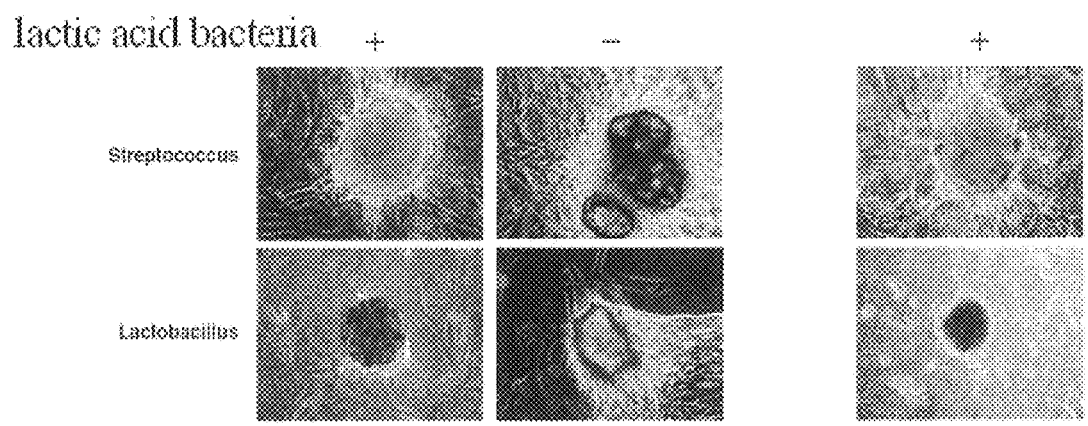
FIG. 5 shows the results of examination attained by infecting the HDF cells with lactic acid bacteria or *Lactobacillus* sp. and inspecting whether or not the formed cell mass can be maintained for a long period of time.

HDF cells ($5\times10^5$ cells/2 ml) were infected with lactic acid bacteria ($2\times10^7$ cells) (i.e., *Streptococcus salivarius* subsp. *thermophilus* (JCM20026) or *Lactobacillus* sp. (JCM20061)) in a 6-well plate, culture was conducted in an incubator at 34° C. in the presence of 5% $CO_2$, half of the culture solution was exchanged every 5 days, and whether or not the cell masses could be maintained for a long period of time was investigated. Culture was conducted with the use of a fibroblast growth medium (Cell Applications, Inc.) to which lactic acid bacteria had been added or had not been added. In FIG. 5, the four photographs on the left show the conditions 30 days after the initiation of culture and the two photographs on the right show the conditions 50 days after the initiation of culture.

As a result, the cell masses were found to be maintained 50 days later if they had been cultured in the presence of lactic acid bacteria, while the cell masses that had been cultured in the absence of lactic acid bacteria were found to have undergone cell death, as shown in FIG. 5. This indicates that lactic acid bacteria are necessary for the maintenance of the cell masses.

Example 6

HDF cells ($5\times10^5$ cells/2 ml) were infected with lactic acid bacteria ($2\times10^7$ cells) (i.e., *Lactococcus lactis* subsp. *Lactis* (JCM20101)) in a 6-well plate, and the cell masses that had formed 8 days layer were subjected to culture on a glass cover coated with poly-L-lysine and laminin (Sigma, 50 µg/ml) for 7 days. The cell masses were fixed with 4% PFA at room temperature for 15 minutes, followed by staining thereof with a mouse anti-α-SMA antibody (Sigma, a vascular marker), a rabbit anti-Desmin antibody (Thermo, a mesoderm marker), a mouse anti-Tuj1 antibody (R&D, a nerve cell marker), and a rabbit anti-GFAP antibody (Dako, a glial cell marker).

Figure 6:
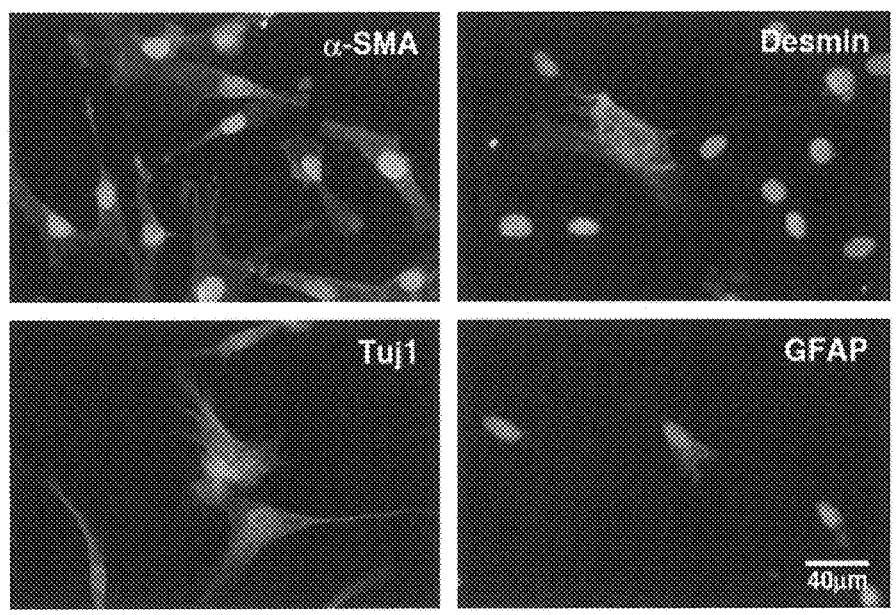
FIG. 6 shows the results of staining attained by infecting the HDF cells with lactic acid bacteria and staining the resultants with the anti-α-SMA antibody (a vascular marker), the anti-Desmin antibody (a mesoderm marker), the anti-Tuj1 antibody (a nerve cell marker), and the anti-GFAP antibody (a glial cell marker), respectively.

As a result, it was found that the differentiated cells could be recognized by relevant antibodies, as shown in FIG. 6. This indicates that the HDF cells were differentiated into various types of cells.

Example 7

HDFs ($5\times10^5$ cells/2 ml) were infected with lactic acid bacteria ($2\times10^7$ cells) (i.e., *Lactobacillus acidophilus* (JCM1021)) in a 6-well plate, and the resulting cell masses were transferred to a 4-well plate 2 weeks later. Culture solutions that induce HDF cells to differentiate into bone cells (B: A shows a 96-well plate after staining with B), fat cells (C), and cartilage cells (D) (GIBCO; A10072-01, A10070-01, and A10071-01) were added in amounts of 500 µl each, half of the culture solution was exchanged every 3 days, and culture was conducted for an additional 2 weeks. In order to examine cell differentiation, the cells on each plate were subjected to staining with Alizarin Red S (bone cells), Oil Red O (fat cells), and Alcian Blue (cartilage cells).

Figure 7:
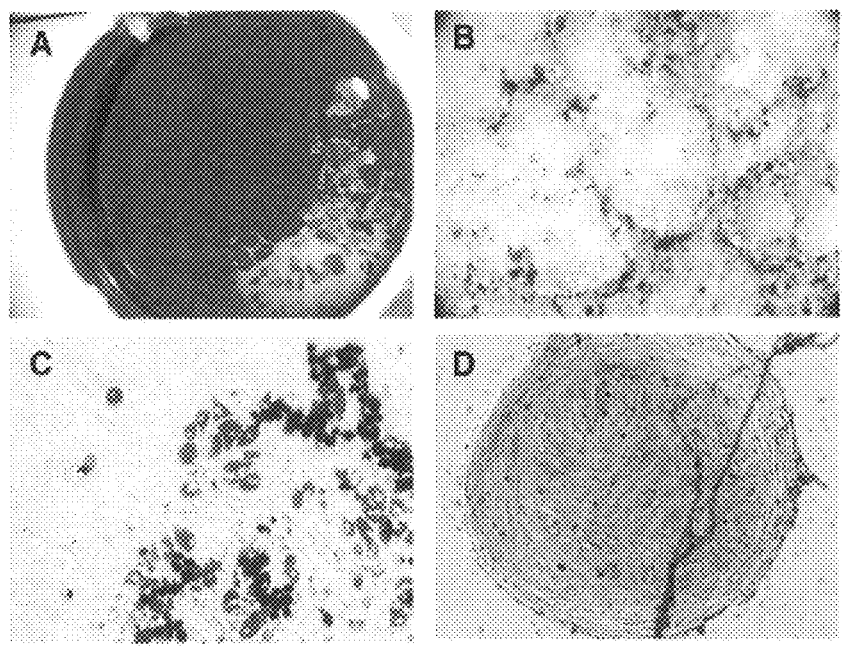
FIG. 7 shows the results of culture attained by infecting the HDF cells with lactic acid bacteria and culturing the resultants with a culture solution that induces the cells to differentiate into bone cells, fat cells, or cartilage cells.

As a result, the cell masses infected with lactic acid bacteria were found to be stained with Alizarin Red S (bone cells), Oil Red O (fat cells), and Alcian Blue (cartilage cells), as shown in FIG. 7. Thus, cell differentiation was confirmed.

Example 8

HDF cells ($5\times10^5$ cells/2 ml) were infected with lactic acid bacteria ($2\times10^7$ cells) (i.e., *Lactobacillus acidophilus* (JCM1021)) in a 6-well plate, half of the culture solution was exchanged every 5 days, and the formed cell masses were observed under an electron microscope in accordance with a conventional resin embedding method for ultrathin sectioning (Tokai Electron Microscopy was commissioned to perform the observation).

Figure 8:
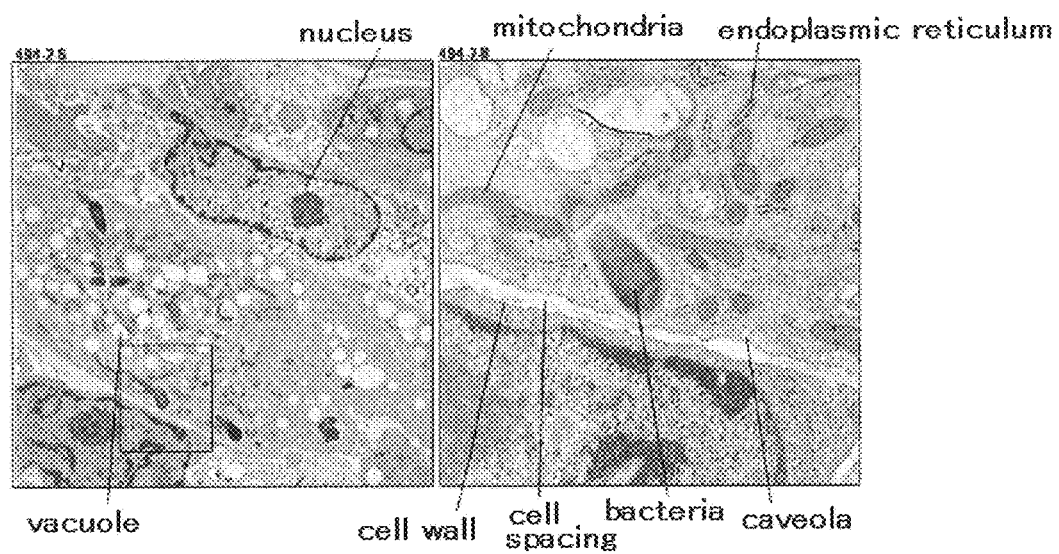
FIG. 8 shows the results of observation attained by infecting the HDF cells with lactic acid bacteria and observing the formed cell mass under an electron microscope.

As a result, the presence of lactic acid bacteria was observed in the cytoplasm (the red arrow in the left diagram), as shown in FIG. 8. The right diagram is an enlarged view showing the framed region in the left diagram.

Example 9 tRNAs were purified from the control HDF cells (C-HDF) and the 20 HDF cell masses infected with lactic acid bacteria (*Lactobacillus acidophilus* (JCM1021)) (Bala-HDF) with the use of a Trizol reagent (Invitrogen), and microarray-based gene expression analysis was performed (Agilent Whole Genome (4×44K) Human; type: one-color). Since this experiment was performed with the addition of lactoferrin (25 µg/ml) in order to improve the efficiency for cell mass formation, the cells were indicated with the term "Bala-HDF." Oncomics Co., Ltd. was commissioned to perform the analysis.

Figures 1, 9:
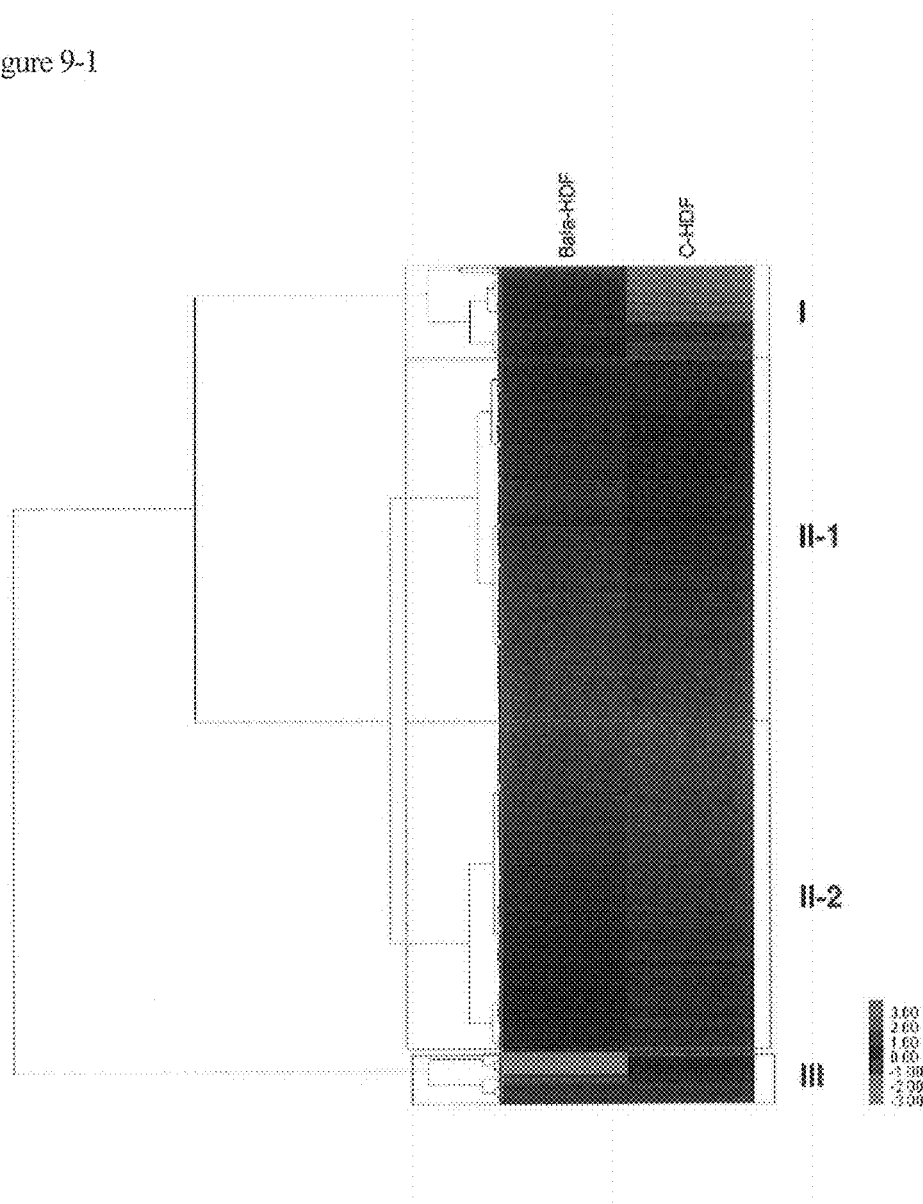
FIG. 9 shows the results of microarray-based gene expression analysis of tRNAs purified from the control HDF cells (C-HDF) and from the HDF cells infected with lactic acid bacteria (Bala-HDF).
Figures 2, 9:
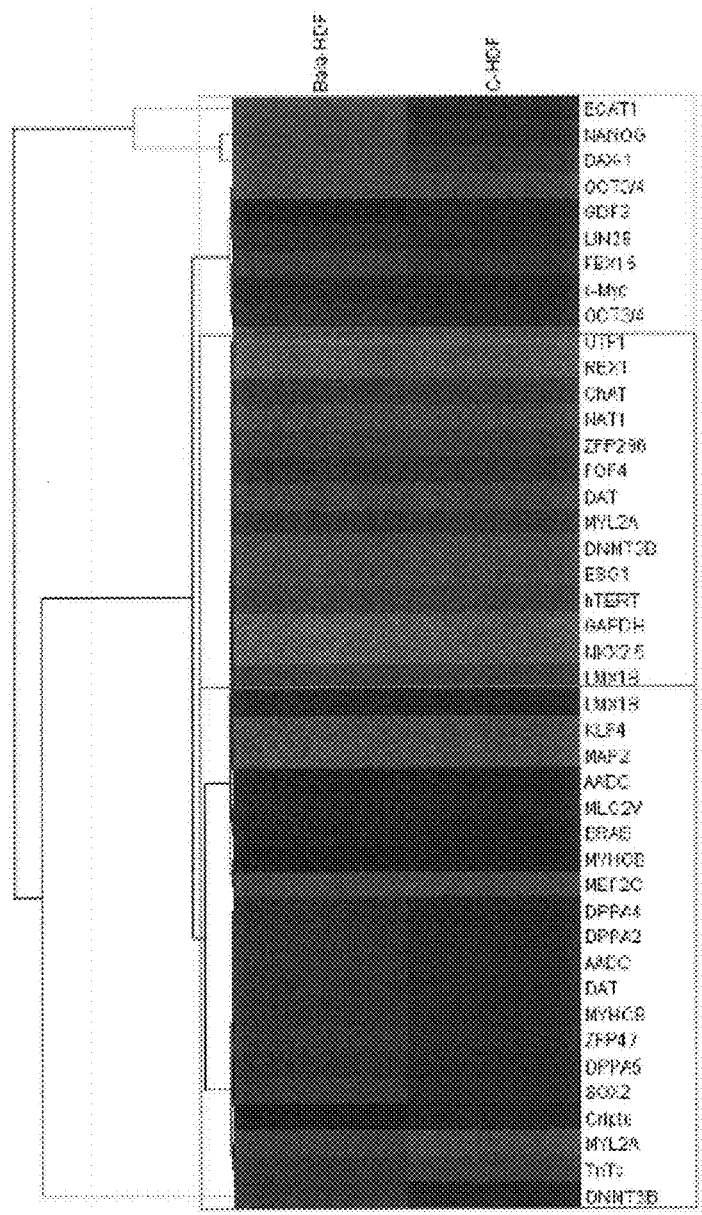

The results are shown in FIG. 9.

FIG. 9-1 shows the results of cluster analysis of the genes exhibiting two-or-more-fold increases/decreases in gene expression levels. The group of genes exhibiting an increased expression level in Bala-HDF compared with that in C-HDF was designated as Group I, the group of genes exhibiting substantially the same expression levels in both C-HDF and Bala-HDF was designated as Group II, and the group of genes exhibiting a decreased expression level in Bala-HDF compared with that in C-HDF was designated as Group III. FIG. 9-2 shows the results of analysis conducted while paying attention to the group of genes that had been reported to be involved with the pluripotency of stem cells.

There were 108 genes exhibiting expression levels increased by 30 or more fold in Bala-HDF compared with that in C-HDF. In contrast, there were 126 genes exhibiting the expression levels decreased by 30 or more fold in Bala-HDF compared with that in C-HDF (Table 1). Concerning the genes related to the pluripotent stem cells, the expression level of the Nanog gene was increased by 8.5 fold and that of the Oct3/4 gene was increased by 2.7 fold in Bala-HDF compared with that in C-HDF. It should be noted that 19 types of Hox genes (i.e., the Homeotic genes) which play a key role in the determination of the structure along the body axis of every animal (Nos. 1 to 4, 6, 8, 10, 13, 14, 17, 18, 22, 35, 47, 53, 59, 74, 117, and 121 in Table 1) are present in the genes which shows the expression levels decreased by 30 or more times in Bala-HDF compared with that in C-HDF.

TABLE 1

126 Genes exhibiting expression levels decreased by 30 or more fold in Lip cells than in HDFs

| no | ProbeName | UniGeneID | GeneSymbol | GeneName | Description | Fold change [Bala-HGF] vs [C-HGF] | Regulation [Bala-HaF] vs [C-HGF] | raw data [Bala-HGF] | raw data [C-HGF] | Flag [Bala-HGF] | Flag [C-HGF] |
|---|---|---|---|---|---|---|---|---|---|---|---|
| 1 | A_24_P124558 | Hs.664500 | HOXC8 | homeobox C8 | Homo sapiens homeobox C8 (HOXC8), mRNA [NM_022658] | 594.18225 | down | 4.66344 | 2869.18900 | Compromised | Detected |
| 2 | A_23_P500998 | Hs.659350 | HOXA9 | homeobox A9 | Homo sapiens homeobox A9 (HOXA9), mRNA [NM_152739] | 592.35516 | down | 3.55414 | 2179.96880 | Compromised | Detected |
| 3 | A_23_P70968 | Hs.660918 | HOXA7 | homeobox A7 | Homo sapiens homeobox A7 (HOXA7), mRNA [NM_006896] | 547.44600 | down | 5.21965 | 3525.65870 | Compromised | Detected |
| 4 | A_23_P363316 | Hs.654456 | HOXB5 | homeobox B5 | Homo sapiens homeobox B5 (HOXB5), mRNA [NM_002147] | 489.89343 | down | 3.73538 | 1894.82500 | Compromised | Detected |
| 5 | A_33_P3341686 | Hs.529901 | XIST | X (inactive)-specific transcript (non-protein coding) | Homo sapiens X (inactive)-specific transcript (non-protein coding) (XIST), non-coding RNA [NR_001564] | 406.94977 | down | 17.06895 | 7192.51030 | Detected | Detected |
| 6 | A_23_P66682 | Hs.98428 | HOXB6 | homeobox B6 | Homo sapiens homeobox B6 (HOXB6), mRNA [NM_018952] | 385.91574 | down | 44.43997 | 17758.20900 | Detected | Detected |
| 7 | A_23_P148541 | Hs.534310 | CTAG1A | cancer/testis antigen 1A | Homo sapiens cancer/testis antigen 1A (CTAG1A), mRNA [NM_139250] | 249.25270 | down | 93.85477 | 24223.07800 | Detected | Detected |
| 8 | A_33_P3300965 | Hs.549040 | HOXC6 | homeobox C6 | Homo sapiens homeobox C6 (HOXC6), transcript variant 2, mRNA [NM_153693] | 247.46118 | down | 33.13974 | 8491.59500 | Detected | Detected |
| 9 | A_23_P7727 | Hs.2799 | HAPLN1 | hyaluronan and proteoglycan link protein 1 | Homo sapiens hyaluronan and proteoglycan link protein 1 (HAPLN1), mRNA [NM_001884] | 241.03157 | down | 2.67364 | 667.28190 | Compromised | Detected |
| 10 | A_24_P77904 | Hs.110637 | HOXA10 | homeobox A10 | Homo sapiens homeobox A10 (HOXA10), transcript variant 1, mRNA [NM_018951] | 212.57760 | down | 2.51297 | 553.14400 | Compromised | Detected |
| 11 | A_23_P7313 | Hs.313 | SPP1 | secreted phosphoprotein 1 | Homo sapiens secreted phosphoprotein 1 (SPP1), transcript variant 1, mRNA [NM_001040058] | 170.12749 | down | 5.62395 | 990.71533 | Compromised | Detected |
| 12 | A_23_P374695 | Hs.89640 | TEK | TEK tyrosine kinase, endothelial | Homo sapiens TEK tyrosine kinase, endothelial (TEK), mRNA [NM_000459] | 168.16338 | down | 4.01029 | 698.29730 | Compromised | Detected |
| 13 | A_23_P3264528 | Hs.249171 | HOXA11 | homeobox A11 | Homo sapiens homeobox A11 (HOXA11), mRNA [NM_005523] | 135.72766 | down | 2.86949 | 403.27990 | Compromised | Detected |
| 14 | A_33_P3300975 | Hs.549040 | HOXC4 | homeobox C4 | Homo sapiens homeobox C4 (HOXC4), transcript variant 1, mRNA [NM_014620] | 131.16129 | down | 7.26983 | 987.33136 | Compromised | Detected |
| 15 | A_24_P264943 | Hs.1584 | COMP | cartilage oligomeric matrix protein | Homo sapiens cartilage oligomeric matrix protein (COMP), mRNA [NM_000095] | 126.96592 | down | 308.84100 | 40602.72700 | Detected | Detected |
| 16 | A_23_P256956 | Hs.718626 | KIF20A | kinesin family member 20A | Homo sapiens kinesin family member 20A (KIF20A), mRNA [NM_005733] | 124.42455 | down | 18.31738 | 2359.94800 | Detected | Detected |
| 17 | A_23_P25150 | Hs.658823 | HOXC9 | homeobox C9 | Homo sapiens homeobox C9 (HOXC9), mRNA [NM_006897] | 122.49983 | down | 52.65937 | 6679.50440 | Detected | Detected |

TABLE 1-continued

126 Genes exhibiting expression levels decreased by 30 or more fold in Lip cells than in HDFs

| no | ProbeName | UniGeneID | GeneSymbol | GeneName | Description | Fold change [Bala-HGF] vs [C-HGF] | Regulation [Bala-HaF] vs [C-HGF] | raw data [Bala-HGF] | raw data [C-HGF] | Flag [Bala-HGF] | Flag [C-HGF] |
|---|---|---|---|---|---|---|---|---|---|---|---|
| 18 | A_24_P218805 | Hs.44276 | HOXC10 | homeobox C10 | Homo sapiens homeobox C10 (HOXG10), mRNA [NM_017409] | 116.49500 | down | 2.27947 | 274.98307 | Compromised | Detected |
| 19 | A_23_P51085 | Hs.421956 | SPC25 | SPC25, NDC80 kinetochore complex component homolog (S. cerevisiae) | Homo sapiens SPC25, NDC80 kinetochore complex component, homolog (S. cerevisiae) (SPC25), mRNA [NM_020675] | 111.57378 | down | 98.13633 | 11337.70200 | Detected | Detected |
| 20 | A_24_P319613 | Hs.153704 | NEK2 | NIMA (never in mitosis gene a)-related kinase 2 | Homo sapiens NIMA (never in mitosis gene a)-related kinase 2 (NEK2), mRNA [NM_002497] | 107.40808 | down | 3.01208 | 334.99344 | Compromised | Detected |
| 21 | A_33_P3318343 | Hs.87225 | CTAG2 | cancer/testis antigen 2 | Homo sapiens cancer/testis antigen 2 (CTAG2), transcript variant 2, mRNA [NM_020994] | 104.32980 | down | 62.47739 | 6749.38800 | Detected | Detected |
| 22 | A_23_P55281 | Hs.436181 | HOXB7 | homeobox B7 | Homo sapiens homeobox B7 (HOXB7), mRNA [NM_004502] | 98.93823 | down | 2.50469 | 256.59653 | Compromised | Detected |
| 23 | A_23_P35219 | Hs.153704 | NEK2 | NIMA (never in mitosis gene a)-related kinase 2 | Homo sapiens NIMA (never in mitosis gene a)-related kinase 2 (NEK2), mRNA [NM_002497] | 96.84769 | down | 12.15671 | 1219.09720 | Detected | Detected |
| 24 | A_33_P3276918 | Hs.592116 | FAM64A | family with sequence similarity 64, member A | Homo sapiens family with sequence similarity 64, member A (FAM64A), mRNA [NM_019013] | 95.78413 | down | 21.28121 | 2110.68300 | Detected | Detected |
| 25 | A_33_P3421243 | Hs.518808 | AFP | alpha-fetoprotein | Homo sapiens alpha-fetoprotein (AFP), mRNA [NM_001134] | 91.34399 | down | 4.93107 | 466.39575 | Compromised | Detected |
| 26 | A_23_P1118174 | Hs.592049 | PLK1 | polo-like kinase 1 (Drosophila) | Homo sapiens polo-like kinase 1 (Drosophila) (PLK1), mRNA [NM_005030] | 91.00964 | down | 27.14974 | 2558.50440 | Detected | Detected |
| 27 | A_23_P43164 | Hs.409602 | SULF1 | sulfatase 1 | Homo sapiens sulfatase 1 (SULF1), transcript variant 3, mRNA [NM_015170] | 87.87735 | down | 242.28316 | 22046.17600 | Detected | Detected |
| 28 | A_23_P118815 | Hs.514527 | BIRC5 | baculoviral IAP repeat-containing 5 | Homo sapiens baculoviral IAP repeat-containing 5 (BIRC5), transcript variant 3, mRNA [NM_001012271] | 84.09252 | down | 897.69434 | 78166.19500 | Detected | Detected |
| 29 | A_23_P118842 | Hs.534499 | KRTAP1-5 | keratin associated protein 1-5 | Homo sapiens keratin associated protein 1-5 (KRTAP1-5), mRNA [NM_031957] | 82.79930 | down | 69.21690 | 5934.33300 | Detected | Detected |
| 30 | A_23_P3307495 | Hs.24553 | STRA6 | stimulated by retinoic acid gene 6 homolog (mouse) | Homo sapiens stimulated by retinoic acid gene 6 homolog (mouse) (STRA6), transcript variant 1, mRNA [NM_001142617] | 81.89140 | down | 24.68651 | 2093.29790 | Detected | Detected |
| 31 | A_23_P79302 | Hs.357567 | LYPD6B | LY6/PLAUR domain containing 6B | Homo sapiens LY6/PLAUR domain containing 6B (LYPD6B), mRNA [NM_177964] | 81.38724 | down | 2.33069 | 196.41484 | Compromised | Detected |
| 32 | A_23_P88331 | Hs.77695 | DLGAP5 | discs, large (Drosophila) homolog-associated protein 5 | Homo sapiens discs, large (Drosophila) homolog-associated protein 5 (DLGAP5), transcript variant 1, mRNA [NM_014750] | 80.77577 | down | 74.09805 | 6197.56400 | Detected | Detected |

TABLE 1-continued

126 Genes exhibiting expression levels decreased by 30 or more fold in Lip cells than in HDFs

| no | ProbeName | UniGeneID | GeneSymbol | GeneName | Description | Fold change [Bala-HGF] vs [C-HGF] | Regulation [Bala-HaF] vs [C-HGF] | raw data [Bala-HGF] | raw data [C-HGF] | Flag [Bala-HGF] | Flag [C-HGF] |
|---|---|---|---|---|---|---|---|---|---|---|---|
| 33 | A_33_P3387524 | Hs.445098 | DEPDC1 | DEP domain containing 1 | *Homo sapiens* DEP domain containing 1 (DEPDC1), transcript variant 1, mRNA [NM_001114120] | 78.75519 | down | 2.93570 | 239.39984 | Compromised | Detected |
| 34 | A_33_P3245218 | Hs.631957 | ODZ2 | odz, odd Oz/ten-m homolog 2 (*Drosophila*) | *Homo sapiens* odz, odd Oz/ten-m homolog 2 (*Drosophila*) (ODZ2), mRNA [NM_001122679] | 78.10015 | down | 5.73433 | 463.73224 | Compromised | Detected |
| 35 | A_23_P370588 | Hs.514292 | HOXB8 | homeobox B8 | *Homo sapiens* homeobox B8 (HOXB8), mRNA [NM_024016] | 76.56639 | down | 2.33384 | 185.03010 | Compromised | Detected |
| 36 | A_32_P96719 | Hs.123253 | SHCBP1 | SHC SH2-domain binding protein 1 | *Homo sapiens* SHC SH2-domain binding protein 1 (SHCBP1), mRNA [NM_024745] | 75.35630 | down | 49.26647 | 3844.18380 | Detected | Detected |
| 37 | A_23_P141624 | Hs.247934 | KRTAP1-1 | keratin associated protein 1-1 | *Homo sapiens* keratin associated protein 1-1 (KRTAP1-1), mRNA [NM_030987] | 72.33463 | down | 2.34718 | 177.01785 | Compromised | Detected |
| 38 | A_23_P65757 | Hs.194698 | CCNB2 | cyclin B2 | *Homo sapiens* cyclin B2 (CCNB2), mRNA [NM_004701] | 71.74918 | down | 487.13727 | 36191.06200 | Detected | Detected |
| 39 | A_23_P35871 | Hs.523526 | E2F8 | E2F transcription factor 8 | *Homo sapiens* E2F transcription factor 8 (E2F8), mRNA [NM_024680] | 71.73170 | down | 2.91475 | 216.49382 | Compromised | Detected |
| 40 | A_33_P3288159 | Hs.121028 | ASPM | asp (abnormal spindle) homolog, microcephaly associated (*Drosophila*) | *Homo sapiens* asp (abnormal spindle) homolog, microcephaly associated (*Drosophila*) (ASPM), mRNA [NM_018136] | 71.65447 | down | 38.55512 | 2860.60820 | Detected | Detected |
| 41 | A_24_P323598 | Hs.99480 | ESCO2 | establishment of cohesion 1 homolog 2 (*S. cerevisiae*) | *Homo sapiens* establishment of cohesion 1 homolog 2 (*S. cerevisiae*) (ESCO2), mRNA [NM_001017420] | 89.80357 | down | 4.74371 | 342.86966 | Compromised | Detected |
| 42 | A_23_P107421 | Hs.515122 | TK1 | thymidine kinase 1, soluble | *Homo sapiens* thymidine kinase 1, soluble (TK1), mRNA [NM_003258] | 68.75995 | down | 1940.31380 | 138146.73000 | Detected | Detected |
| 43 | A_33_P3291831 | Hs.14559 | CEP55 | centrosomal protein 55 kDa | *Homo sapiens* centrosomal protein 55 kDa (CEP55), transcript variant 1, mRNA [NM_018131] | 68.03040 | down | 19.57336 | 1378.80080 | Detected | Detected |
| 44 | A_23_P155711 | Hs.405467 | NEIL3 | nei endonuclease VIII-like 3 (*E. coli*) | *Homo sapiens* nei endonuclease VIII-like 3 (*E. coli*) (NEIL3), mRNA [NM_018248] | 67.63126 | down | 3.82752 | 268.03870 | Compromised | Detected |
| 45 | A_23_P215634 | Hs.450230 | IGFBP3 | Insulin-like growth factor binding protein 3 | *Homo sapiens* insulin-like growth factor binding protein 3 (IGFBP3), transcript variant 1, mRNA [NM_001013398] | 67.36516 | down | 1824.75790 | 127283.97000 | Detected | Detected |
| 46 | A_23_P45011 | Hs.486798 | PPP1R14C | protein phosphatase 1, regulatory (inhibitor) subunit 14C | *Homo sapiens* protein phosphatase 1, regulatory (inhibitor) subunit 14C (PPP1R14C), mRNA [NM_030949] | 66.81310 | down | 29.65725 | 2051.75500 | Detected | Detected |
| 47 | A_23_P316511 | Hs.654560 | HOXB3 | homeobox B3 | *Homo sapiens* homeobox B3 (HOXB3), mRNA [NM_002146] | 65.99564 | down | 2.28753 | 156.32037 | Compromised | Detected |

TABLE 1-continued

126 Genes exhibiting expression levels decreased by 30 or more fold in Lip cells than in HDFs

| no | ProbeName | UniGeneID | GeneSymbol | GeneName | Description | Fold change [Bala-HGF] vs [C-HGF] | Regulation [Bala-HaF] vs [C-HGF] | raw data [Bala-HGF] | raw data [C-HGF] | Flag [Bala-HGF] | Flag [C-HGF] |
|---|---|---|---|---|---|---|---|---|---|---|---|
| 48 | A_23_P52017 | Hs.121028 | ASPM | asp (abnormal spindle) homolog, microcephaly associated (Drosophila) | Homo sapiens asp (abnormal spindle) homolog, microcephaly associated (Drosophila) (ASPM), mRNA [NM_018136] | 65.81075 | down | 157.07414 | 10703.71700 | Detected | Detected |
| 49 | A_23_P126212 | Hs.175613 | CLSPN | claspin homolog (Xenopus laevis) | Homo sapiens claspin homolog (Xenopus laevis) (CLSPN), mRNA [NM_022111] | 65.52806 | down | 2.25390 | 152.93062 | Compromised | Detected |
| 50 | A_23_P138507 | Hs.334562 | CDC2 | cell division cycle 2, G1 to S and G2 to M | Homo sapiens cell division cycle 2, G1 to S and G2 to M (CDC2), transcript variant 1, mRNA [NM_001786] | 62.70113 | down | 119.53158 | 7760.52200 | Detected | Detected |
| 51 | A_23_P398854 | Hs.122110 | DOK7 | docking protein 7 | Homo sapiens docking protein 7 (DOK7), transcript variant 1, mRNA [NM_173660] | 62.14818 | down | 2.55532 | 164.43954 | Compromised | Detected |
| 52 | A_24_P37253 | Hs.21929 | LYPD6 | LY6/PLAUR domain containing 6 | Homo sapiens LY6/PLAUR domain containing 6 (LYPD6), mRNA [NM_194317] | 62.11988 | down | 2.63021 | 169.18219 | Compromised | Detected |
| 53 | A_23_P3271273 | Hs.514289 | HOXB2 | homeobox B2 | Homo sapiens homeobox B2 (HOXB2), mRNA [NM_002145] | 60.37445 | down | 23.25287 | 1453.65990 | Detected | Detected |
| 54 | A_33_P3313075 | Hs.714179 | LOC100129619 | hypothetical LOC100129619 | PREDICTED: Homo sapiens hypothetical LOC100129619 (LOC100129619), mRNA [XM_001717266] | 59.50954 | down | 5.94992 | 366.63214 | Compromised | Detected |
| 55 | A_23_P34788 | Hs.720061 | KIF2C | kinesin family member 2C | Homo sapiens kinesin family member 2C (KIF2C), mRNA [NM_006845] | 58.41870 | down | 273.92862 | 16853.63900 | Detected | Detected |
| 56 | A_24_P299474 | Hs.631957 | ODZ2 | odz, odd Oz/ten-m homolog 2 (Drosophila) | Homo sapiens odz, odd Oz/ten-m homolog 2 (Drosophila) (ODZ2), mRNA [NM_001122679] | 58.33110 | down | 17.59517 | 1062.73900 | Detected | Detected |
| 57 | A_23_P70249 | Hs.856 | CDC25C | cell division cycle 25 homolog C (S. pombe) | Homo sapiens cell division cycle 25 homolog C (S. pombe) (CDC25C), transcript variant 1, mRNA [NM_001790] | 58.22949 | down | 30.77745 | 1855.70400 | Detected | Detected |
| 58 | A_23_P115872 | Hs.14559 | CEP55 | centrosomal protein 55 kDa | Homo sapiens centrosomal protein 55 kDa (CEP55), transcript variant 1, mRNA [NM_018131] | 57.81258 | down | 178.33205 | 10675.41700 | Detected | Detected |
| 59 | A_33_P3377529 | Hs.533357 | HOXA4 | homeobox A4 | Homo sapiens homeobox A4 (HOXA4), mRNA [NM_002141] | 57.78450 | down | 6.40620 | 383.30520 | Compromised | Detected |
| 60 | A_33_P3807062 | Hs.532968 | HJURP | Holliday junction recognition protein | Homo sapiens Holliday junction recognition protein (HJURP), mRNA [NM_018410] | 56.66154 | down | 274.61868 | 16112.07700 | Detected | Detected |
| 61 | A_23_P57588 | Hs.386189 | GTSE1 | G-2 and S-phase expressed 1 | Homo sapiens G-2 and S-phase expressed 1 (GTSE1), mRNA [NM_016426] | 56.62428 | down | 44.89710 | 2632.41300 | Detected | Detected |
| 62 | A_24_P225616 | Hs.226390 | RRM2 | ribonucleotide reductase M2 | Homo sapiens ribonucleotide reductase M2 (RRM2), transcript variant 2, mRNA [NM_001034] | 56.30852 | down | 70.34309 | 4101.36700 | Detected | Detected |

TABLE 1-continued

126 Genes exhibiting expression levels decreased by 30 or more fold in Lip cells than in HDFs

| no | ProbeName | UniGeneID | GeneSymbol | GeneName | Description | Fold change [Bala-HGF] vs [C-HGF] | Regulation [Bala-HaF] vs [C-HGF] | raw data [Bala-HGF] | raw data [C-HGF] | Flag [Bala-HGF] | Flag [C-HGF] |
|---|---|---|---|---|---|---|---|---|---|---|---|
| 63 | A_23_P259586 | Hs.169340 | TTK | TTK protein kinase | *Homo sapiens* TTK protein kinase (TTK), transcript variant 1, mRNA [NM_003318] | 56.15061 | down | 25.58659 | 1487.64700 | Detected | Detected |
| 64 | A_24_P297539 | Hs.93002 | UBE2C | ubiquitin-conjugating enzyme E2C | *Homo sapiens* ubiquitin-conjugating enzyme E2C (UBE2CX transcript variant 6, mRNA [NM_181803] | 55.08201 | down | 533.38605 | 30421.77100 | Detected | Detected |
| 65 | A_23_P212844 | Hs.104019 | TACC3 | transforming, acidic coiled-coil containing protein 3 | *Homo sapiens* transforming, acidic coiled-coil containing protein 3 (TACC3), mRNA [NM_006342] | 53.95437 | down | 57.68809 | 3222.89280 | Detected | Detected |
| 66 | A_24_P346855 | Hs.80976 | MKI67 | antigen identified by monoclonal antibody Ki-67 | *Homo sapiens* antigen identified by monoclonal antibody Ki-67 (MKI67), transcript variant 1, mRNA [NM_002417] | 53.93493 | down | 12.88017 | 718.32430 | Compromised | Detected |
| 67 | A_23_P210176 | Hs.133397 | ITGA6 | integrin, alpha 6 | *Homo sapiens* integrin, alpha 6 (ITGA6), transcript variant 2, mRNA [NM_000210] | 53.34168 | down | 21.47094 | 1185.90750 | Detected | Detected |
| 68 | A_33_P3258627 | | | | Putative uncharacterized protein ENSP00000387024 [Source: UniProtKB/TrEMBL; Acc; B8ZZ63] [ENST00000409162] | 52.59529 | down | 2.31702 | 126.18560 | Compromised | Detected |
| 69 | A_23_P10206 | Hs.159226 | HAS2 | hyaluronan synthase 2 | *Homo sapiens* hyaluronan synthase 2 (HAS2), mRNA [NM_005328] | 51.20701 | down | 50.60540 | 2683.23930 | Detected | Detected |
| 70 | A_33_P3216008 | Hs.88523 | SKA3 | spindle and kinetochore associated complex subunit 3 | *Homo sapiens* spindle and kinetochore associated complex subunit 3 (SKA3), transcript variant 1, mRNA [NM_145061] | 50.93999 | down | 12.93789 | 682.42560 | Detected | Detected |
| 71 | A_23_P423237 | Hs.37167 | SGCG | sarcoglycan, gamma (35 kDa dystrophin-associated glycoprotein) | *Homo sapiens* sarcoglycan, gamma (35 kDa dystrophin-associated glycoprotein) (SGCG), mRNA [NM_000231] | 50.23103 | down | 2.61723 | 136.12785 | Compromised | Detected |
| 72 | A_23_P24129 | Hs.40499 | DKK1 | dickkopf homolog 1 (*Xenopus laevis*) | *Homo sapiens* dickkopf homolog 1 (*Xenopus laevis*) (DKK1), mRNA [NM_012242] | 49.39177 | down | 971.48020 | 49684.58200 | Detected | Detected |
| 73 | A_23_P163567 | Hs.368421 | SMPD3 | sphingomyelin phosphodiesterase 3, neutral membrane (neutral sphingomyelinase II) | *Homo sapiens* sphingomyelin phosphodiesterase 3, neutral membrane (neutral sphingomyelinase II) (SMPD3), mRNA [NM_018667] | 49.28304 | down | 18.40829 | 939.38586 | Detected | Detected |
| 74 | A_24_P416370 | Hs.664706 | HOXB4 | homeobox B4 | *Homo sapiens* homeobox B4 (HOXB4), mRNA [NM_024015] | 48.99025 | down | 21.78193 | 1104.94100 | Detected | Detected |
| 75 | A_24_P225970 | Hs.105153 | SGOL1 | shugoshin-like 1 (*S. pombe*) | *Homo sapiens* shugoshin-like 1 (SGOL1), transcript variant A1, mRNA [NM_001012409] | 48.72279 | down | 10.13061 | 511.09410 | Compromised | Detected |

TABLE 1-continued

126 Genes exhibiting expression levels decreased by 30 or more fold in Lip cells than in HDFs

| no | ProbeName | UniGeneID | GeneSymbol | GeneName | Description | Fold change [Bala-HGF] vs [C-HGF] | Regulation [Bala-HaF] vs [C-HGF] | raw data [Bala-HGF] | raw data [C-HGF] | Flag [Bala-HGF] | Flag [C-HGF] |
|---|---|---|---|---|---|---|---|---|---|---|---|
| 76 | A_24_P347378 | Hs.507658 | ALOX5AP | arachidonate 5-lipoxygenase-activating protein | *Homo sapiens* arachidonate 5-lipoxygenase-activating protein (ALOX5AP), mRNA [NM_001629] | 48.64382 | down | 2.26967 | 114.32042 | Compromised | Detected |
| 77 | A_33_P3387831 | Hs.208912 | CENPM | centromere protein M | *Homo sapiens* centromere protein M (CENPM), transcript variant 1, mRNA [NM_024053] | 47.62641 | down | 238.83578 | 11778.23800 | Detected | Detected |
| 78 | A_23_P356684 | Hs.62180 | ANLN | anillin, actin binding protein | *Homo sapiens* anillin, actin binding protein (ANLN), mRNA [NM_018685] | 46.97221 | down | 89.14799 | 4335.96440 | Detected | Detected |
| 79 | A_33_P3330149 | Hs.270303 | PAX6 | paired box 6 | *Homo sapiens* paired box 6 (PAX6), transcript variant 1, mRNA [NM_000280] | 46.52534 | down | 2.62064 | 126.24968 | Compromised | Detected |
| 80 | A_24_P30557 | Hs.381715 | TBX5 | T-box5 | *Homo sapiens* T-box 5 (TBX5), transcript variant 1, mRNA [NM_000192] | 45.04174 | down | 4.14714 | 193.41812 | Compromised | Detected |
| 81 | A_23_P146274 | Hs.521651 | STMN2 | stathmin-like 2 | *Homo sapiens* stathmin-like 2 (STMN2), mRNA [NM_007029] | 43.26243 | down | 251.80971 | 11280.19100 | Detected | Detected |
| 82 | A_33_P3303956 | Hs.658061 | LOC100133311 | similar to hCG1644697 | PREDICTED: *Homo sapiens* similar to hCG1644697 (LOC100133311), mRNA [XM_002344295] | 43.11292 | down | 2.59771 | 115.96621 | Compromised | Detected |
| 83 | A_23_P130182 | Hs.442658 | AURKB | aurora kinase B | *Homo sapiens* aurora kinase B (AURKB), mRNA [NM_004217] | 42.91836 | down | 24.55805 | 1091.36500 | Detected | Detected |
| 84 | A_23_P56347 | Hs.654413 | PSG3 | pregnancy specific beta-1-glycoprotein 3 | *Homo sapiens* pregnancy specific beta-1-glycoprotein 3 (PSG3), mRNA [NM_021016] | 42.86491 | down | 93.47945 | 4149.07400 | Detected | Detected |
| 85 | A_23_P122197 | Hs.23960 | CCNB1 | cyclin B1 | *Homo sapiens* cyclin B1 (CCNB1), mRNA [NM_031966] | 42.74203 | down | 517.57600 | 22906.70500 | Detected | Detected |
| 86 | A_23_P100127 | Hs.181855 | CASC5 | cancer susceptibility candidate 5 | *Homo sapiens* cancer susceptibility candidate 5 (CASC5), transcript variant 1, mRNA [NM_170589] | 42.70049 | down | 13.65018 | 603.63723 | Detected | Detected |
| 87 | A_24_P280983 | Hs.387427 | HOXA11AS | HOXA11 antisense RNA (non-protein coding) | *Homo sapiens* HOXA11 antisense RNA (non-protein coding) (HOXA11AS), antisense RNA [NR_002795] | 41.97556 | down | 34.17975 | 1485.58810 | Detected | Detected |
| 88 | A_23_P74349 | Hs.851950 | NUF2 | NUF2, NDC80 kinetochore complex component, homolog (*S. cerevisiae*) | *Homo sapiens* NUF2, NDC80 kinetochore complex component, homolog (*S. cerevisiae*) (NUF2), transcript variant 1, mRNA [NM_145697] | 41.75897 | down | 109.18320 | 4720.18600 | Detected | Detected |
| 89 | A_23_P373521 | Hs.388245 | HAND2 | heart and neural crest derivatives expressed 2 | *Homo sapiens* heart and neural crest derivatives expressed 2 (HAND2), mRNA [NM_021973] | 41.60090 | down | 13.50888 | 581.90924 | Detected | Detected |
| 90 | A_33_P3311498 | Hs.363603 | LOC283392 | hypothetical LOC283392 | *Homo sapiens* hypothetical LOC283392 (LOC283392), transcript variant 1, non-coding RNA [NR_026837] | 41.49494 | down | 5.94969 | 255.63634 | Compromised | Detected |

TABLE 1-continued

126 Genes exhibiting expression levels decreased by 30 or more fold in Lip cells than in HDFs

| no | ProbeName | UniGeneID | GeneSymbol | GeneName | Description | Fold change [Bala-HGF] vs [C-HGF] | Regulation [Bala-HaF] vs [C-HGF] | raw data [Bala-HGF] | raw data [C-HGF] | Flag [Bala-HGF] | Flag [C-HGF] |
|---|---|---|---|---|---|---|---|---|---|---|---|
| 91 | A_23_P151150 | Hs.239 | FOXM1 | forkhead box M1 | Homo sapiens forkhead box M1 (FOXM1), transcript variant 1, mRNA [NM_202002] | 41.37134 | down | 121.89368 | 5221.72360 | Detected | Detected |
| 92 | A_23_P148475 | Hs.548326 | KIF4A | kinesin family member 4A | Homo sapiens kinesin family member 4A (KIF4A), mRNA [NM_012310] | 41.30457 | down | 83.02992 | 3551.12330 | Detected | Detected |
| 93 | A_23_P68610 | Hs.244580 | TPX2 | TPX2, microtubule-associated, homolog (Xenopus laevis) | Homo sapiens TPX2, microtubule-associated, homolog (Xenopus laevis) (TPX2), mRNA [NM_012112] | 41.25013 | down | 243.59319 | 10404.55600 | Detected | Detected |
| 94 | A_24_P140475 | Hs.655143 | SORBS2 | sorbin and SH3 domain containing 2 | Homo sapiens sorbin and SH3 domain containing 2 (SORBS2), transcript variant 2, mRNA [NM_021669] | 41.04034 | down | 6.06472 | 257.72375 | Compromised | Detected |
| 95 | A_23_P124417 | Hs.469649 | BUB1 | budding uninhibited by benzimidazoles 1 homolog (yeast) | Homo sapiens budding uninhibited by benzimidazoles 1 homolog (yeast) (BUB1), mRNA [NM_004336] | 40.92328 | down | 63.01636 | 2670.28000 | Detected | Detected |
| 96 | A_23_P70007 | Hs.720052 | HMMR | hyaluronan-mediated motility receptor (RHAMM) | Homo sapiens hyaluronan-mediated motility receptor (RHAMM) (HMMR), transcript variant 2, mRNA [NM_012484] | 40.85090 | down | 116.10930 | 4911.35940 | Detected | Detected |
| 97 | A_32_P150891 | Hs.283127 | DIAPH3 | diaphanous homolog 3 (Drosophila) | Homo sapiens diaphanous homolog 3 (Drosophila) (DIAPH3), transcript variant 1, mRNA [NM_001042517] | 40.27765 | down | 13.45490 | 561.14830 | Detected | Detected |
| 98 | A_33_P3708413 | Hs.512842 | MFAP5 | microfibrillar associated protein 5 | Homo sapiens microfibrillar associated protein 5 (MFAP5), mRNA [NM_003480] | 39.62058 | down | 356.31840 | 14618.14000 | Detected | Detected |
| 99 | A_23_P96325 | Hs.47558 | ERCC6L | excision repair cross-complementing rodent repair deficiency, complementation group 6-like | Homo sapiens excision repair cross-complementing rodent repair deficiency, complementation grasp 6-like (ERCC6L), mRNA [NM_017669] | 39.58863 | down | 20.08920 | 823.50500 | Detected | Detected |
| 100 | A_23_P167159 | Hs.7122 | SCRG1 | stimulator of chondrogenesis 1 | Homo sapiens stimulator of chondrogenesis 1 (SCRG1), mRNA [NM_007281] | 39.33724 | down | 2.66140 | 108.40463 | Compromised | Detected |
| 101 | A_23_P121795 | Hs.655143 | SORBS2 | sorbin and SH3 domain containing 2 | Homo sapiens sorbin and SH3 domain containing 2 (SORBS2), transcript variant 2, mRNA [NM_021069] | 38.97343 | down | 13.70106 | 552.91187 | Detected | Detected |
| 102 | A_23_P215454 | Hs.647061 | ELN | elastin | Homo sapiens elastin (ELN), transcript variant 1, mRNA [NM_000501] | 37.86731 | down | 51.50940 | 2019.68640 | Detected | Detected |
| 103 | A_23_P117852 | Hs.81892 | KIAA0101 | KIAA0101 | Homo sapiens KIAA0101 (KIAA0101), transcript variant 1, mRNA [NM_014736] | 36.88694 | down | 540.27780 | 20635.85700 | Detected | Detected |
| 104 | A_23_P72668 | Hs.26530 | SDPR | serum deprivation response | Homo sapiens serum deprivation response (SDPR), mRNA [NM_004657] | 36.05926 | down | 4.32851 | 161.66243 | Compromised | Detected |

TABLE 1-continued

126 Genes exhibiting expression levels decreased by 30 or more fold in Lip cells than in HDFs

| no | ProbeName | UniGeneID | GeneSymbol | GeneName | Description | Fold change [Bala-HGF] vs [C-HGF] | Regulation [Bala-HaF] vs [C-HGF] | raw data [Bala-HGF] | raw data [C-HGF] | Flag [Bala-HGF] | Flag [C-HGF] |
|---|---|---|---|---|---|---|---|---|---|---|---|
| 105 | A_23_P323751 | Hs.472716 | FAM83D | family with sequence similarity 83, member D | Homo sapiens family with sequence similarity 83, member D (FAM83D), mRNA [NM_030919] | 35.86057 | down | 68.57602 | 2546.37650 | Detected | Detected |
| 106 | A_33_P3326210 | Hs.99480 | ESCO2 | establishment of cohesion 1 homolog 2 (S. cerevisiae) | Homo sapiens establishment of cohesion 1 homolog 2 (S. cerevisiae) (ESCO2), mRNA [NM_001017420] | 35.85314 | down | 2.66392 | 98.89648 | Compromised | Detected |
| 107 | A_23_P157136 | Hs.655515 | SCIN | scinderin | Homo sapiens scinderin (SCIN), transcript variant 2, mRNA [NM_033128] | 35.78193 | down | 2.38629 | 88.41367 | Compromised | Detected |
| 108 | A_23_P375 | Hs.524571 | CDCA8 | cell division cycle associated 8 | Homo sapiens cell division cycle associated 8 (CDCA8), mRNA [NM_018101] | 35.73556 | down | 524.05695 | 19391.53300 | Detected | Detected |
| 109 | A_23_P50108 | Hs.414407 | NDC80 | NDC80 homolog, kinetochore complex component (S. cerevisiae) | Homo sapiens NDC80 homolog, kinetochore complex component (NDC80), mRNA [NM_006101] | 35.48090 | down | 492.26477 | 18085.33000 | Detected | Detected |
| 110 | A_32_P62997 | Hs.104741 | PBK | PDZ binding kinase | Homo sapiens PDZ binding kinase (PBK), mRNA [NM_018492] | 35.46259 | down | 272.00460 | 9988.02700 | Detected | Detected |
| 111 | A_32_P140489 | Hs.492277 | GDF6 | growth differentiation factor 6 | Homo sapiens growth differentiation factor 5 (GDF6), mRNA [NM_001001557] | 34.81978 | down | 3.73760 | 134.75726 | Compromised | Detected |
| 112 | A_33_P3272957 | Hs.658061 | LOC100133311 | similar to hCG1644697 | PREDICTED: Homo sapiens similar to hCG1644697 (LOC100133311), mRNA [XM_002344295] | 34.80172 | down | 2.87419 | 103.57362 | Compromised | Detected |
| 113 | A_23_P163481 | Hs.513645 | BUB1B | budding uninhibited by benzimidazoles 1 homolog beta (yeast) | Homo sapiens budding uninhibited by benzimidazoles 1 homolog beta (yeast) (BUB1B), mRNA [NM_001211] | 34.57169 | down | 88.89745 | 3182.31400 | Detected | Detected |
| 114 | A_33_P3311755 | Hs.270845 | KIF23 | kinesin family member 23 | Homo sapiens kinesin family member 23 (KIF23), transcript variant 1, mRNA [NM_138555] | 34.17050 | down | 84.03610 | 2973.37900 | Detected | Detected |
| 115 | A_23_P200310 | Hs.445098 | DEPDC1 | DEP domain containing 1 | Homo sapiens DEP domain containing 1 (DEPDC1), transcript variant 2, mRNA [NM_017779] | 34.04056 | down | 70.18784 | 2473.95400 | Detected | Detected |
| 116 | A_23_P58321 | Hs.58974 | CCNA2 | cyclin A2 | Homo sapiens cyclin A2 (CCNA2), mRNA [NM_001237] | 33.80436 | down | 59.81775 | 2093.80300 | Detected | Detected |
| 117 | A_23_P501538 | Hs.659337 | HOXA3 | homeobox A3 | Homo sapiens homeobox A3 (HOXA3), transcript variant 2, mRNA [NM_153631] | 33.35369 | down | 2.40679 | 83.12165 | Compromised | Detected |
| 118 | A_33_P3423585 | Hs.657273 | UNC13C | unc-13 homolog C (C. elegans) | Homo sapiens unc-13 homolog C (UNC13C), mRNA [NM_001080534] | 33.21877 | down | 2.73679 | 94.13646 | Compromised | Detected |

TABLE 1-continued

126 Genes exhibiting expression levels decreased by 30 or more fold in Lip cells than in HDFs

| no | ProbeName | UniGeneID | GeneSymbol | GeneName | Description | Fold change [Bala-HGF] vs [C-HGF] | Regulation [Bala-HaF] vs [C-HGF] | raw data [Bala-HGF] | raw data [C-HGF] | Flag [Bala-HGF] | Flag [C-HGF] |
|---|---|---|---|---|---|---|---|---|---|---|---|
| 119 | A_24_P399888 | Hs.208912 | CENPM | centromere protein M | *Homo sapiens* centromere protein M (CENPM), transcript variant 2, mRNA [NM_001002876] | 32.49764 | down | 30.25951 | 1018.23220 | Detected | Detected |
| 120 | A_24_P66027 | Hs.226307 | APOBEC3B | apolipoprotein B mRNA editing enzyme, catalytic polypeptide-like 3B | *Homo sapiens* apolipoprotein B mRNA editing enzyme, catalytic polypeptide-like 3B (APOBEC3B), mRNA [NM_004900] | 31.39611 | down | 82.84677 | 2693.29900 | Detected | Detected |
| 121 | A_23_P107283 | Hs.514289 | HOXB2 | homeobox B2 | *Homo sapiens* homeobox B2 (HOXB2), mRNA [NM_002145] | 31.19959 | down | 256.95248 | 8301.08400 | Detected | Detected |
| 122 | A_33_P3368358 | Hs.37982 | NEDD9 | neural precursor cell expressed, developmentally down-regulated 9 | *Homo sapiens* neural precursor cell expressed, developmentally down-regulated 9 (NEDD9), transcript variant 2, mRNA [NM_182966] | 31.14883 | down | 5.83776 | 188.28748 | Compromised | Detected |
| 123 | A_33_P3255824 | | | | | 31.06368 | down | 4.28859 | 137.94330 | Compromised | Detected |
| 124 | A_23_P96158 | Hs.2785 | KRT17 | keratin 17 | *Homo sapiens* keratin 17 (KRT17), mRNA [NM_000422] | 30.95973 | down | 2.61022 | 83.67714 | Compromised | Detected |
| 125 | A_33_P3242649 | Hs.301052 | KIF18A | kinesin family member 18A | *Homo sapiens* kinesin family member 18A (KIF18A), mRNA [NM_031217] | 30.24299 | down | 21.10955 | 661.05370 | Detected | Detected |
| 126 | A_33_P3270514 | Hs.61435 | NBLA00301 | Nbla00301 | *Homo sapiens* Nbla00301 (NBLA00301), non-coding RNA [NR_003679] | 30.17527 | down | 4.17646 | 130.49452 | Compromised | Detected |

Example 10

HDF cells ($5\times10^5$ cells/2 ml) were infected with lactic acid bacteria ($2\times10^7$ cells) (i.e., *Lactobacillus acidophilus* (JCM1021)) in a 6-well plate, and the cell masses were collected 2 weeks later, followed by treatment with trypsin. The cells ($5\times10^5$ cells/30 µl) were administered to one of the testes of a male SCID mouse (9-to-10 week-old), and the formation of teratoma was examined 3 months later.

Figure 10:
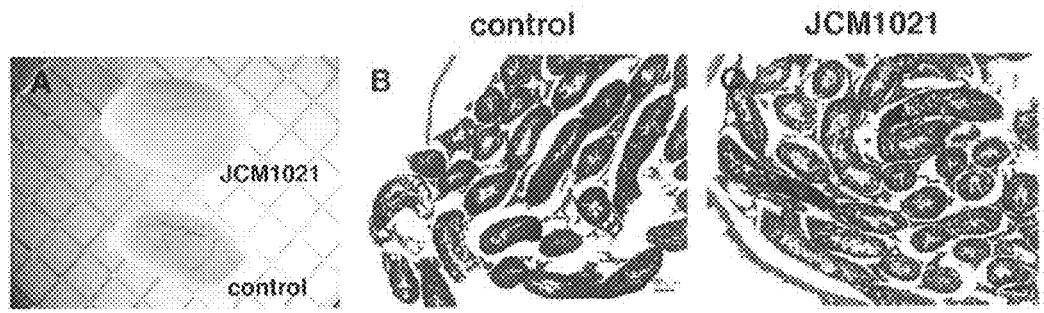
FIG. 10 shows the results attained by infecting the HDF cells with lactic acid bacteria, administering the resultants to one of the testes of an SCID mouse, and inspecting the formation of teratoma 3 months later.

As a result, the testis that had been infected with lactic acid bacteria (above) were found to have become somewhat larger than the control testis (below, another testis of the same mouse), as shown in the photograph of FIG. 10, but teratoma formation was not observed. Paraffin sections (6 µl) were prepared and subjected to HE staining. No differences were observed in the structure of the testis into which the JCM1021-infected HDFs had been transplanted or the control testis.

Example 11

Mouse embryonic fibroblasts (MEF cells) were sampled in accordance with the sampling method developed by the RIKEN Center for Developmental Biology. A 12.5-day-old GFP mouse embryo was extracted from the uterus, and the head, the caudal portion, the extremities, and the visceral organ were removed. The remaining tissue was cut into small pieces with the use of surgical scissors, and the resultant was incubated in a 0.25% trypsin-EDTA solution at 37° C. for 15 minutes. After the incubation product had been filtered through a cell strainer, the remnant was suspended in a cell culture solution, and the cells constituting one embryo were seeded in a 10-cm petri dish. After the cells reached confluence, the cells were infected with lactic acid bacteria (JCM1021), as with the case of the HDF cells, and culture was then conducted for 5 days.

Figure 11:
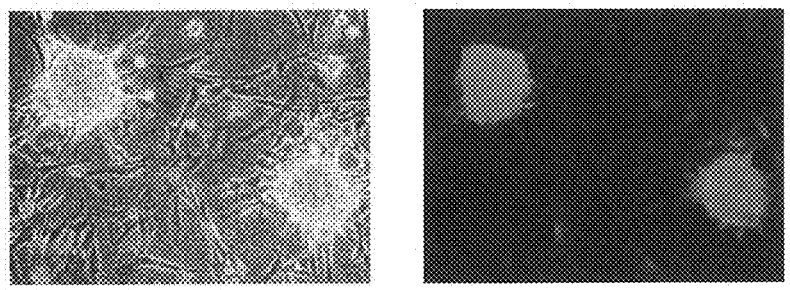
FIG. 11 shows the results attained by isolating mouse embryonic fibroblasts from E12.5 GFP mouse embryos, infecting the cells with lactic acid bacteria (JCN1021), and culturing the cells for 5 days.

As a result, the MEF cells that had been infected with lactic acid bacteria were found to have formed cell masses, as shown in the photograph of FIG. 11.

Example 12

Breast cancer cells (MCF7; RBRC-RCB1904), lung cancer cells (A549; RBRC-RCB0098), and hepatic cancer cells (HEP G2; RBRC-RCB1648) were obtained from the RIKEN BioResource Center. In the same manner as in Example 1, lactic acid bacteria (i.e., *Lactococcus lactis* subsp. *Lactis* (JCM20101)) were introduced into a 6-well plate at $1\times10^8$ cells/well in advance, and $5\times10^5$ cancer cells were added thereto. Culture was conducted in such state in an incubator at 34° C. in the presence of 5% $CO_2$.

Figure 12:
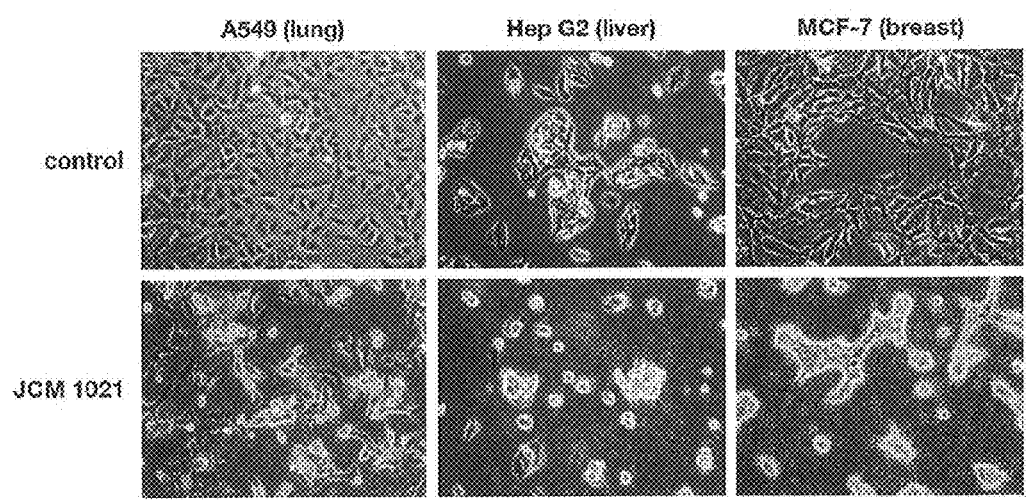
FIG. 12 shows the results attained by infecting breast cancer cells (MCF7), hepatic cancer cells (HepG2), or lung cancer cells (A549) with lactic acid bacteria (JCM1021) and conducting culture for 4 days.

The results are shown in FIG. 12. Cell masses were observed several days later, as shown in FIG. 12. These photographs show the conditions 4 days after the initiation of culture.

Example 13

The experiment was carried out in the same manner as in Example 1, except that commercially available yogurt was introduced into a 6-well plate at 50 µl/well in advance, and $5\times10^5$ cancer cells were added thereto. Culture was conducted in an incubator at 34° C. in the presence of 5% $CO_2$.

Figure 13:
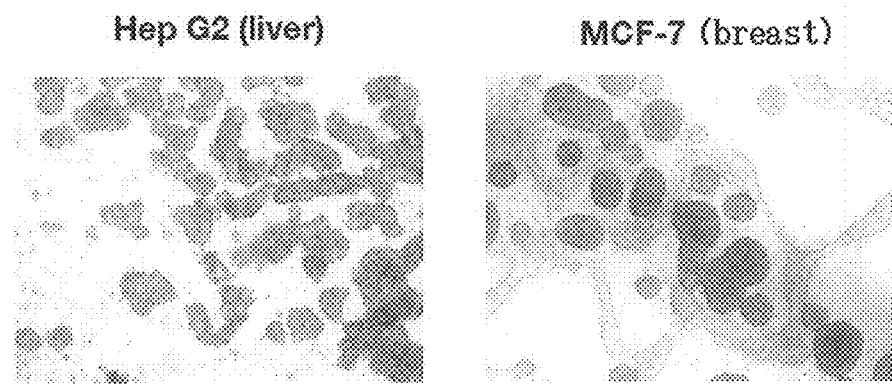
FIG. 13 shows the results of cell culture conducted with the addition of yogurt to hepatic cancer cells (HepG2) and breast cancer cells (MCF7) for 9 days.

The results are shown in FIG. 13. Cell masses were observed several days later, as shown in FIG. 13. These photographs show the conditions 9 days after the initiation of culture.

Example 14

The experiment was carried out in the same manner as in Example 12 with the use of hepatic cancer cells (HEP G2) and lactic acid bacteria (JCM20101). The cells were recovered 4, 8, and 12 days after infection, and then RT-PCR was carried out by using c-Myc and the carcino embryonic antigen (CEA) as cancer cell markers.

Figure 14:
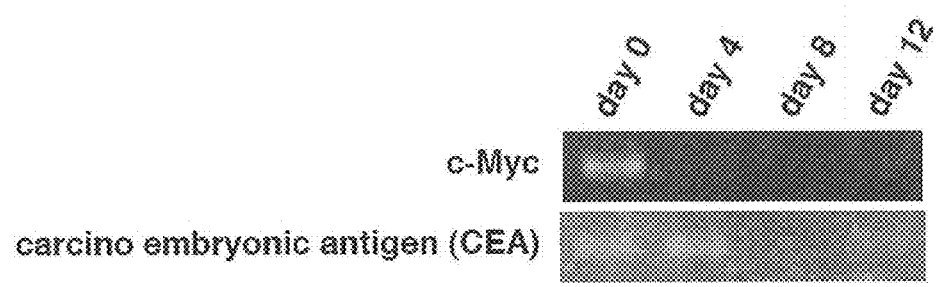
FIG. 14 shows the results of RT-PCR attained by infecting hepatic cancer cells (HepG2) with lactic acid bacteria (JCM1021), recovering the cells 4, 8, and 12 days thereafter, and conducting RT-PCR with the use of c-Myc and CEA cancer cell markers.

The results are shown in FIG. 14. While both marker molecules were expressed on Day 0, the c-Myc expression level was decreased from Day 4, and the CEA expression level was decreased from Day 8, as shown in FIG. 14.

Example 15

Figure 15:
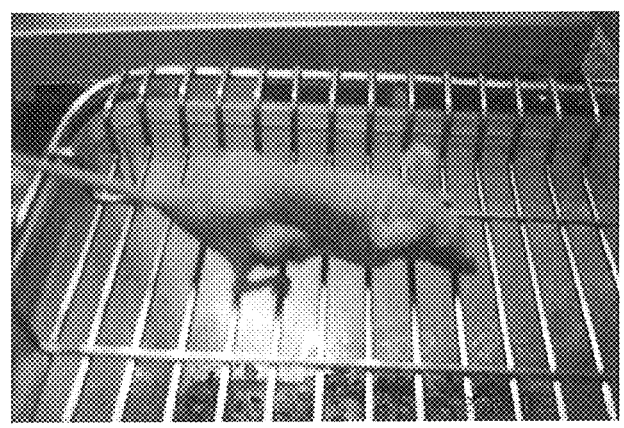
FIG. 15 shows the results attained by preparing cell masses of lung cancer cells (A549), transplanting the resulting cell masses hypodermically to 8-week-old female nude mice, and observing tumor formation approximately 1 month later.

According to the hanging drop method, cells are treated with trypsin, the treated cells are suspended in a culture solution at $1\times10^5$ cells/20 µl, the cell suspension is added dropwise onto the lid of a petri dish, the lid is overturned, and the petri dish is then allowed to stand overnight. On the following day, a cell mass is observed at the tip of a drop, and the resulting cell mass is transplanted into a mouse. The hanging drop method was carried out using lung cancer cells (A549) to form cell masses. The resulting 5 cell masses were transplanted hypodermically to an 8-week-old female nude mouse. Tumor formation was observed approximately 1 month later (FIG. 15). The tumors were extracted and trimmed to the size of 4×4 mm each. Control tumor masses were soaked in a PBS solution. The test tumor masses were soaked in a solution of lactic acid bacteria (JCM20101) ($1\times10^8$/ml) at room temperature for 20 minutes. Thereafter, a single tumor mass was transplanted hypodermically to an 8-week-old female nude mouse. A solution containing lactic acid bacteria was injected into the target mouse of lactic acid bacteria test on Day 3 and Day 6. The tumor was extracted and weighed 40 days later.

Figure 16:
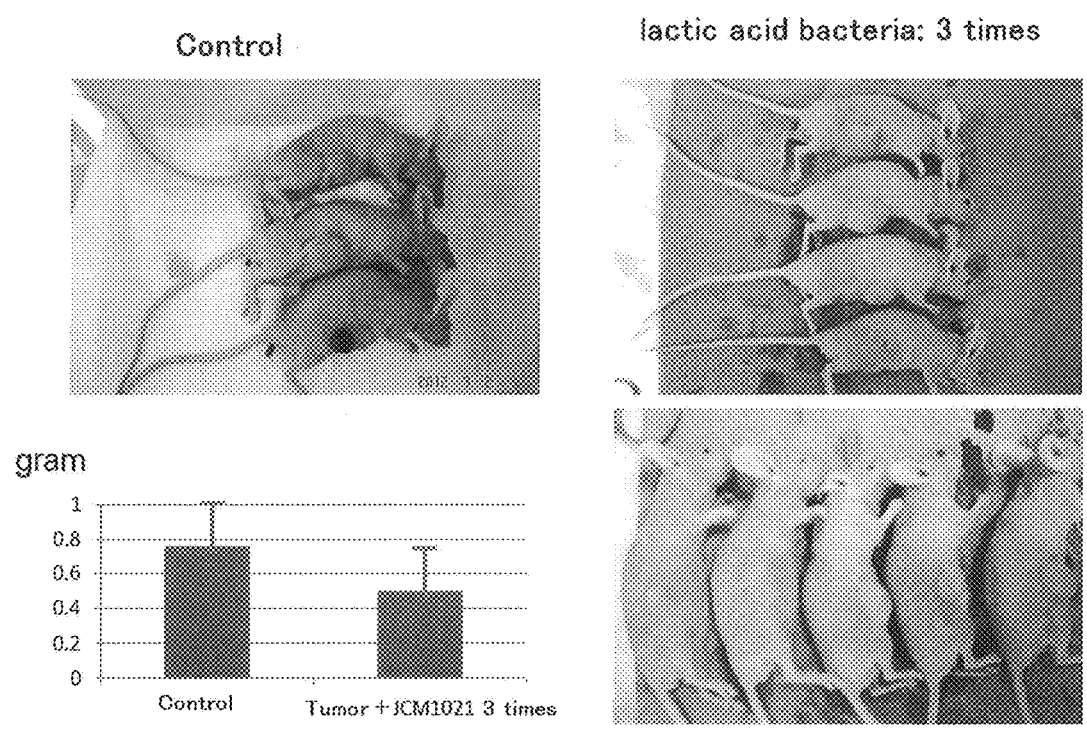
FIG. 16 shows the results of measurement of the weight of tumors extracted 40 days after hypodermic transplantation thereof. Control mice were subjected to tumor transplantation in the absence of lactic acid bacteria (JCM1021), and the target mice subjected to lactic acid bacteria injection 3 times were subjected to tumor transplantation in the presence of lactic acid bacteria ($2\times10^8$ in 0.2 ml each), followed by further lactic acid bacteria injection on Day 3 and Day 6.

The results are shown in FIG. 16. In comparison with the mouse into which the tumor had been transplanted, a reduction in tumor size was observed in the mouse which was infected with lactic acid bacteria and further injected with lactic acid bacteria.

Example 16

In the same manner as in Example 1, *Bacillus subtilis* var. *natto* or *E. coli* (XL1-blue, Stratagene) cells were introduced into a 6-well plate at $1\times10^8$ cells/well in advance, and $5\times10^5$ HDF cells (Cell Applications, Inc., Cat No. 106-05a) were added thereto. Culture was conducted in an incubator at 34° C. in the presence of 5% $CO_2$.

Figure 17:
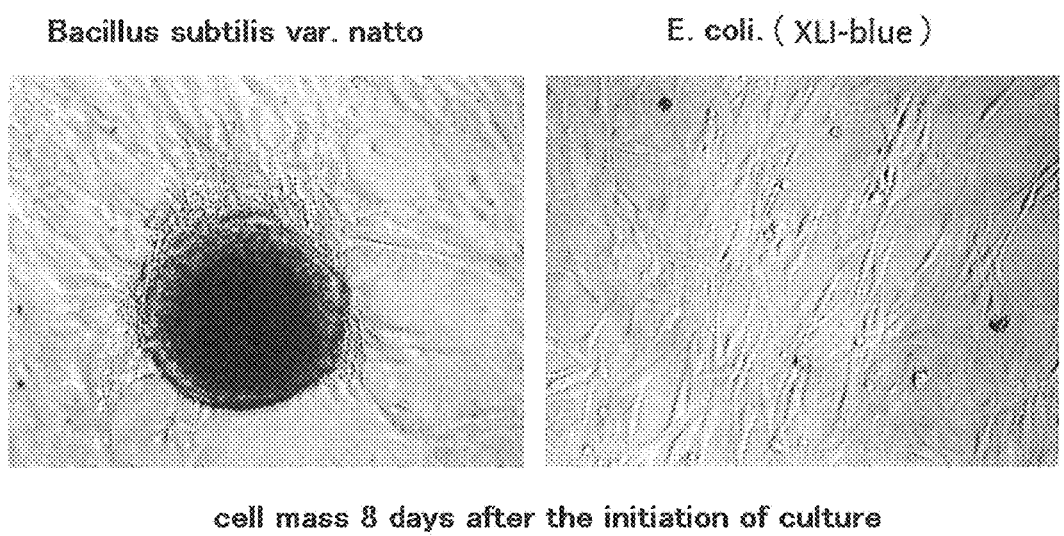
FIG. 17 shows HDF cells cultured together with *Bacillus subtilis* var. *natto* or *E. coli*.

The results are shown in FIG. 17. While a cell mass was observed several days later in the presence of *Bacillus subtilis* var. *natto*, formation of a cell mass was not observed in the presence of *E. coli*, as shown in FIG. 17. These photographs show the conditions 8 days after the initiation of culture.

The invention claimed is:

1. A method for altering the expression profile of fibroblasts, comprising treating fibroblasts with trypsin, bringing whole and live bacteria having fermentation ability into contact with fibroblasts in vitro, and culturing the fibroblasts, wherein the expression profile of the fibroblasts is altered and the altered expression comprises increased expression of Nanog and Oct3/4, and wherein the bacteria having fermentation ability are *Lactococcus lactis, Streptococcus salivarius, Lactobacillus* sp., or *Lactobacillus acidophilus*.

2. The method according to claim 1, wherein the fibroblasts are derived from a mammal.

3. The method according to claim 1, wherein the fibroblasts are derived from a human or mouse.

4. The method according to claim 1, wherein the bacteria having fermentation ability are *Lactococcus lactis* subsp. *Lactis, Streptococcus salivarius* subsp. *thermophilus, Lactobacillus* sp., or *Lactobacillus acidophilus*.

5. The method according to claim 1, wherein bringing whole and live bacteria having fermentation ability into contact with fibroblasts in vitro comprises infecting the fibroblasts with the bacteria in vitro.

6. A method for producing somatic cells which comprises:
   (a) producing cells by the method according to claim 1; and
   (b) inducing the cells produced in (a) to differentiate.

* * * * *